United States Patent
Rooney

(12) 
(10) Patent No.: US 6,187,744 B1
(45) Date of Patent: *Feb. 13, 2001

(54) METHODS AND COMPOSITIONS FOR REGULATING THE INTRAVASCULAR FLOW AND OXYGENATING ACTIVITY OF HEMOGLOBIN IN A HUMAN OR ANIMAL SUBJECT

(76) Inventor: Michael W. Rooney, 202 Arron Ct., Vernon Hills, IL (US) 60061

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/480,189

(22) Filed: Jun. 7, 1995

Related U.S. Application Data

(63) Continuation-in-part of application No. 07/849,610, filed on Mar. 11, 1992, now abandoned.

(51) Int. Cl.$^7$ ............................. A61K 38/16; A61K 35/14
(52) U.S. Cl. ............................. 514/6; 514/832; 514/833; 530/385; 530/402
(58) Field of Search ............................. 514/6, 832, 833; 530/385; 604/7; 423/374, 405; 424/608

(56) References Cited

U.S. PATENT DOCUMENTS

| | | | | |
|---|---|---|---|---|
| 4,578,395 | * | 3/1986 | Yamaguchi et al. | 514/356 |
| 4,826,811 | * | 5/1989 | Sehgal et al. | 514/6 |
| 5,028,627 | * | 7/1991 | Kilbourn et al. | 514/565 |
| 5,380,758 | * | 1/1995 | Stamler et al. | 514/562 |

OTHER PUBLICATIONS

Martin et al., J. Pharmacol. Exp. Theraputics, vol. 232, No. 3, pp. 708–716, 1985.*
Roonet et al. 1991. Biomater, Artif. Cells Immobilization Biotechnology, 19, 477, Aug. 1991.*
Katusic et al. 1996. Gen. Pharmac. 27, 239, 1996.*
Sharma et al. 1995. Am. J. Physiol. 269, H1379, 1995.*
Boon et al. 1977. Chem. Abstracts 87, 65, 1977.*

* cited by examiner

*Primary Examiner*—Christopher S. F. Low
*Assistant Examiner*—Abdel A. Mohamed
(74) *Attorney, Agent, or Firm*—Duane Morris & Heckscher LLP

(57) ABSTRACT

Methods for time-regulated prophylaxis or treatment of animals or humans for limited circulatory oxygen delivery induced by the inhibitory effects of a plasma-borne hemoglobin-based material on L-arginine→nitric oxide→cGMP pathways in the arteriovenous vasculature. The properties of the invention restore and increase circulatory oxygen delivery by increasing circulatory flow of the blood-hemoglobin-based material through selective activation of L-arginine→nitric oxide→cGMP pathways in the arterial rather than venous vasculature. A method of the invention utilizes oxygen-carrying biocolloid compositions that consist of a hemoglobin-based material and a guanosine 3':5'-cyclic monophosphate (cGMP) generating entity, for treatment of animals and humans in need thereof for diseases or medical conditions which utilize the biocolloids as hemodiluents, blood substitutes, plasma expanders, or resuscitative fluids. The invention provides selective administration of cGMP generating entities for prophylaxis or treatment of animals or humans with limited circulatory oxygen delivery induced by a plasma hemoglobin-based material arising from intravenous administration, disease or medical condition. Most importantly, the invention provides for time-controlled enablement of the oxygen-deliverying properties of the invention that would be used for treatment of specific diseases or medical conditions requiring time-dependent increases in circulatory oxygen delivery.

30 Claims, 14 Drawing Sheets

METHODS AND COMPOSITIONS FOR REGULATING THE INTRAVASCULAR FLOW AND OXYGENATING ACTIVITY OF HEMOGLOBIN IN A HUMAN OR ANIMAL SUBJECT

This is a continuation of patent application Ser. No. 07/849,610, filed Mar. 11, 1992 and now abandoned, the disclosure of which is hereby incorporated herein in its entirety.

A portion of the disclosure of this patent document contains material which is subject to copyright protection. The copyright owner has no objection to the facsimile reproduction by any one of the patent disclosure, as it appears in the Patent & Trademark Office patent files or records, but otherwise reserves all copyright rights whatsoever.

FIELD OF THE INVENTION

The present invention relates generally to compositions that enhance the in vivo oxygenating properties of hemoglobin products. More particularly, the present invention relates to time-controlled superoxygenating compositions that comprise hemoglobin colloid and guanosine 3':5'-cyclic monophosphate (cyclic GMP) generating compounds, and to methods for treatment of diseases or medical conditions which utilize the time-controlled superoxygenating compositions as biocolloids, i.e. hemodiluents, blood substitutes, plasma expanders, or resuscitative fluids.

BACKGROUND

There are many medical conditions, for example hemorrhagic hypotension and anaphylactic shock, in which significant blood loss and/or hypotension (abnormally low blood pressure) occur leading to reduced tissue oxygenation. For patients with such medical conditions, it is desirable and often critical for their survival to stabilize their blood pressure and to increase the amount of oxygen provided to body tissues by their circulatory systems.

Considerable effort has therefore been expended in developing colloidal substances which may be used as resuscitation fluids and/or blood plasma expanders for stabilizing blood pressure by hemodilution (i.e., increasing blood plasma volume) and which are capable of carrying and delivering oxygen to bodily tissues. The costs, risks (including contamination with disease-causing viruses) and histocompatibility requirements associated with the transfusion of whole blood or blood fractions have stimulated researchers to develop alternate oxygen-carrying substances.

Hemoglobin, the natural respiratory protein of erythrocyte which carries oxygen to body tissues from the lungs, is a potential alternate oxygen-carrying biocolloid. Erythrocytes contain approximately 34 grams of hemoglobin per 100 ml of red cells.

Hemodilution experiments with hemoglobin have revealed that unlike hemodilution with albumin, hemodilution with hemoglobin does not augment cardiac output (whole-body blood flow). During hemodilution with inert colloids such as albumin, whole-body blood flow increases inversely proportional to the level of hemodilution. In other words, an ≈50% hemodilution (i.e., an ≈50% decrease in blood red cell mass) increases blood flow ≈100%, and so on. The physical basis of the hematocrit-blood flow inverse relationship is analogous to viscosity-flow mechanics. In other words, decreases in hematocrit cause decreases in blood viscosity which results in increases in blood flow. Hemoglobin, on the other hand, is not inert. Hemodilution with hemoglobin causes vasoconstriction which results in smaller diameter blood vessels. Therefore, even though blood viscosity is decreased during hemodilution with hemoglobin, the smaller diameter blood vessels resist increases in blood flow. This is analogous to direct mechanical relationship between flow and tube diameter, i.e., decreased diameter results in decreased flow. Whole-body flow (cardiac output) is not increased during hemodilution with hemoglobin because flow of the less viscous blood is opposed by the hemoglobin-mediated decrease in blood vessel diameter.

Increased cardiac output is desirable to increase oxygen delivery to the tissues. Examples of publications describing the lack of increased cardiac output during hemodilution with natural (unmodified) hemoglobin are Sunder-Plassmann et al., *Eur. J. Int. Care Med.* 1, 37–42 (1975) and Moss et al., *Surg. Gyn. Ob.*, 142, 357–362 (1976).

Hemodilution with modified hemoglobin that has been polymerized also has failed to increase cardiac output. See Vlahakes et al., *J. Thorac. Cardiovasc. Surg.*, 100, 379–388 (1990) which describes the hemodilution of sheep with polymerized bovine hemoglobin prepared by Biopure Corporation; Rausch et al., supra (assigned to Biopure Corporation), which describes similar experiments; and Gould et al., *Ann. Surg.*, 211, 394–398 (1990) and Hobbhahn et al., *Acta Anaesthesiol. Scand.*, 29, 537–543 (1985) which describe hemodiluting baboons and dogs, respectively, with polymerized human hemoglobin solutions. Thus, hemodilution with both natural and modified hemoglobin has failed to increase cardiac output.

Because cardiac output does not increase upon dilution of the blood with hemoglobin, body tissues are required, as one compensatory mechanism, to extract more oxygen from the diluted blood to prevent tissue damage from hypoxia. However, such compensatory mechanisms have real limits in vivo. The heart, for instance, normally functions at about 95% maximal oxygen extraction levels and thus is only capable of increasing oxygen extraction about 5% (assuming 100% efficiency is possible). In the case of hemodilution with albumin, even though arterial oxygen content is decreased, oxygen delivery is essentially maintained at baseline levels because of low viscosity blood that causes flow (cardiac output) to increase proportionally. Therefore, hemodilution with hemoglobin offers no physiological or clinical advantage over hemodiluting with albumin. In fact, oxygen delivery is suboptimal during hemodilution with hemoglobin. This leads us to the central idea of the invention. If cardiac output or whole-body flow were allowed to increase as blood was diluted with hemoglobin then oxygen delivery would be clinically superior to hemodilution with albumin because of the added arterial oxygen content provided by the plasma hemoglobin colloid.

The mechanism of unchanged cardiac output during hemodilution with hemoglobin may be caused by an inactivation of endogenous nitric oxide (NO), also called endothelium-derived relaxing factor (EDRF), which is an important regulator of blood vessel diameter. For nearly 100 hundred years, it has been known that hemoglobin inactivates NO that has been diffused to the blood via the lungs. Only recently has it been discovered that NO also forms biochemically in vivo. There is, however, uncertainty as to whether oxyHb directly reacts with NO or whether an indirect oxyHb-mediated product such as superoxide is responsible. An overview of the possible molecular interactions of oxyHb with NO and relevant compounds is give below.

Initially, the reaction equations between NO and oxyHb/deoxyHb are simple yielding $$oxyHb + NO \rightarrow metHb + NO_3^-$$

$$deoxyHb + NO \rightarrow NOHb$$

where metHb is ferric($Fe^{3+}$)hemoglobin, $NO_3^-$ is nitrate and NOHb is nitrosylhemoglobin. However, $NO_3^-$ can react with deoxyHb to yield:

$$2deoxyHb + NO_3^- + H_2O \rightarrow 2metHb + NO_2^- + 2OH^-$$

and nitrite ($NO_2^-$) can react with oxyHb or deoxyHb to yield:

$$2oxyHb + NO_2^- + H_2O \rightarrow 2metHb + NO_3^- + 2OH_2^-$$

$$oxyHb + NO_2^- + 2H^+ \rightarrow metHb + NO_2 + H_2O_2$$

$$deoxyHb + NO_2^- + H_2O \leftarrow \rightarrow \tfrac{1}{2}[metHb + NO] + \tfrac{1}{2}[NOHb] + 2OH^{-1}$$

where $NO_2$ is nitrogen dioxide and $H_2O_2$ is hydrogen peroxide. The free energy of activation ($\Delta G$) of the last equation is rather low (−21.23 kJ/mole) and therefore metHb . . . NO can be reduced to deoxyHb. However, in vivo experiments have shown that nitrite exposure results in about an equal amount of NOHb and metHb formed in the blood. Furthermore, the $\Delta G$ of equation 2 is low (−46.02 Kj/mole) and in the presence of $O_2$ will proceed according to the $\Delta G$ of equation 1 ($\approx$−170 Kj/mole). Finally, metHb and $H_2O_2$ can react:

$$metHb + H_2O_2 \rightarrow ferrylhemoglobin + H_2O$$

to produce a spectrophotometrically detectable red compound known as ferryl($Fe^{++++}$)hemoglobin. In many of the above reactions, heme or chelatable iron can be substituted for Hb.

Under physiological conditions, i.e., in an oxygenated and heated aqueous with a pH of about 7.4, NO is rapidly converted to nitrogen dioxide:

$$2NO + O_2 \rightarrow 2NO_2$$

Nitrogen dioxide is quite reactive, and in aqueous solution disproportionates to nitrate and nitrite as:

$$2NO_2 \rightarrow N_2O_4 + H_2O \rightarrow NO_3^- + NO_2^- + 2H^+$$

The decomposition of NO can also occur via:

$$NO_2 + NO \rightarrow N_2O_3 + H_2O \rightarrow 2NO_2^- + 2H^+$$

The abnormally rapid oxidation of oxyHb by NO is consistent with oxyHb serving as a superoxide ($O_2^-$) donor, where $$oxyHb + NO \rightarrow metHb + ONOO^- \rightarrow NO_3^-$$

or as recent studies propose, that NO is inactivated by other sources of $O_2^-$ yielding:

$$NO + O_2^- \rightarrow ONOO^- + H^+ \rightarrow HO\cdot + NO_2 \rightarrow NO_3^- + H^+$$

where $ONOO^-$ is peroxynitrite. Hydroxyl radical (HO.) can further react with $NO_2^-$ to form $NO_2$. Peroxynitrate ($O_2NOO^-$) and $ONOO^-$ are also suspected intermediates in the autocatalytic oxidation of oxyHb by $NO_2$ and NO, respectively.

Considering the autoxidation of oxyHb:

$$oxyHb \leftarrow \rightarrow metHb + O_2^-$$

$$O_2^- + oxyHb \rightarrow metHb + O_2 + H_2O_2$$

These last two equations are slow (the rate constants are $4-6 \times 10^3$ $M^{-1}$ $sec^{-1}$). A currently-popular hypothesis is that $O_2^-$ is converted in the presence of iron to the highly toxic HO. radical via the superoxide driven Fenton reaction:

$$O_2^- + Fe^{3+} \rightarrow Fe^{++} + O_2$$

$$2O_2^- + 2H^+ \rightarrow H_2O_2 + O_2$$

$$H_2O_2 + Fe^{++} \rightarrow HO\cdot + OH^- + Fe^{3+}$$

Whether $oxyHb + H_2O_2$ forms HO. has not been proven. Furthermore, ferric iron ($Fe^{3+}$) is sparingly soluble under physiological conditions and, therefore, must be chelated to heme, ferritin, etc to remain in solution. As with metHb, heme-$Fe^{3+}$ may also react with $H_2O_2$ to form the ferryl-heme radical (.$Fe^{4+}$-heme).

Finally, rather than binding to heme, inactivation of endogenous NO may occur via its reaction with the thiol groups of oxyHb. Recently, it was shown that NO circulates in mammalian plasma primarily as an S-nitroso adduct on the thiol groups of serum albumin.

The biochemical pathway/effect of NO production and metabolism is believed to comprise the following, L-arginine→NO synthase→NO→guanylate cyclase→cyclic GMP→decreased blood vessel diameter. Conceivably, hemoglobin could decrease blood vessel diameter by inactivating any point of the pathway. Furthermore, hemoglobin does not effect the diameter of veins and arteries equally. Equal effect on these two vascular systems is necessary to increase blood flow or cardiac output as observed during albumin hemodilution. Therefore, two mechanisms must be synchronized in order for cardiac output (and oxygenation) to be maximized during hemodilution with hemoglobin: 1) molecular intervention of in vivo hemoglobin chemistry and 2) hemodynamic responsiveness in venous and arterial circulations.

There thus continues to exist a need in the art for new methods, and compositions, useful for hemodilution with hemoglobin which increase cardiac output (oxygen delivery) and give this colloid a clinical advantage over non-oxygenated colloids such albumin.

SUMMARY OF THE INVENTION

The present invention provides therapeutic compositions for hemodilution with hemoglobin products that superaugment the oxygenating capacity of the circulatory system when using these products. The cardiac output-increasing compositions comprise hemoglobin and guanosine 3':5'-cyclic monophosphate (cyclic GMP) generating compounds. Methods of treatment for diseases and medical, conditions requiring/indicating use of a superoxygenating compositions as hemodiluents, blood substitutes, plasma expanders, or resuscitative fluids are described. For use in therapeutic compositions of the present invention, the hemoglobin products may be modified to prevent rapid clearance from the intravascular space in vivo. For example, the hemoglobin products may be cross-linked, chemically modified with compounds such as polyethylene glycol or encapsulated (for example, in liposomes, glucose polymers or gelatin).

Therapeutic compositions according to the invention were formulated to reverse the vasoconstriction of hemoglobin products and to thereby facilitate the flow-increasing effects of diluted blood (augmented cardiac output). The compositions comprise either hemoglobin and cyclic GMP generating compounds or hemoglobin chemically coupled to cyclic GMP-generating compounds. Hemoglobin and excess nitric oxide were discovered to exhibit a combined pharmacology resulting in increased cardiac output in mammals. See Rooney et al., *FASEB Journal*, 5(4), Abstract 158 (1991).

Appropriate cyclic GMP-generating compounds contemplated by the present invention include, for example, nitric oxide precursors which are endogenous to mammals (e.g., L-arginine, lysine, glutamate, ornithine) and engineered compounds which contain nitric oxide groups (e.g., the nitrovasodilators sodium nitroprusside, organic nitrates, S-nitrosothiols, sydnonimines and furoxans) or which cause the release of nitric oxide in vivo (e.g., the endothelium-dependent vasodilators acetylcholine, bradykinin, adenine nucleotides and substance P) or any compound which may directly or indirectly activate guanylate cyclase (dihydropyridines and related nitrovasodilator-dihydropyridine hybrid structures).

Cyclic GMP-generating compounds may be coupled to hemoglobin by chemical processes which selectively attach the compounds to reactive amino (e.g., lysine residues), carboxyl (e.g., glutamate residues) or previously thiolated-amino groups on the hemoglobin surface. Native thiol and disulfide groups of hemoglobin that play an important structural or functional role should be avoided.

Typically, a bifunctional reagent such as an imidoester may be used to couple a cyclic GMP-generating compound to reactive hemoglobin groups. In some cases, a group on the cyclic GMP-generating compound may be activated prior to incubation with hemoglobin. For example, a carboxyl group on the cyclic GMP generating compound may be activated with a carbodi-imide for coupling to amino groups on the hemoglobin surface. Appropriate coupling reactions may involve other reagents, for example, sodium cyanoborohydride, carboxi-imides, succinic anhydride, thiols, N-hydroxysuccinimide and dithiothreitol.

The chemical coupling of the hemoglobin and the cyclic GMP-generating compound may involve a reversible or an irreversible bond. See, for example, the coupling reactions in Carlsson et al., *Biochem. J.*, 173, 723–737 (1978) and Martin et al., *J. Biol. Chem.* 249, 286–288 (1981). It may be useful to react the β or α chain lysines or the amino terminal residues of hemoglobin with agents that increase relative oxygen dissociation [see Chatterjee et al., *J. Biol. Chem.*, 261, 9929–9937 (1986)] before coupling the hemoglobin to the cyclic GMP-generating compounds.

The therapeutic hemoglobin compositions of the present invention may be described as "blood component substitutes." In addition to hemoglobin and cyclic GMP-generating compounds, the compositions may comprise physiologically acceptable plasma substitutes. Suitable plasma substitutes are linear polysaccharides (e.g., dextrans, gum arabic pectins, balanced fluid gelatin, and hydroxyethyl starch), polymeric substitutes (e.g., polyethylene oxide, polyacrylamide, polyvinyl pyrrolidone, polyvinyl alcohol, ethylene oxide-propylene glycol condensate), aqueous solutions (e.g., Lactated Ringers and saline), coacervates (composed of fatty acids, phospholipids, glycerates or cholesterol, for example) and colloidal substitutes (e.g., albumin).

The therapeutic compositions according to the present invention are useful for treatment of diseases or medical conditions in which intravascular or intraosseous administration of a resuscitative fluid or blood plasma expander is indicated/required. Resuscitative fluids and blood plasma expanders are required for treatment of diseases and medical conditions in which there is significant blood loss, hypotension and/or a need to maximize the availability of oxygen to the body tissues. Examples of such diseases and medical conditions are hemorrhagic hypotension, septic shock, cardio-pulmonary bypass, sickle cell and neoplastic anemias, plasma and extracellular fluid loss from burns, stroke, angioplasty, cardioplegia, radiation therapy, acute myocardial infarction, and both routine and lengthy surgical procedures.

Methods of treating such diseases and medical condition according to the present invention comprise the step of hemodiluting a mammal with a pharmaceutically effective amount of a hemoglobin composition according to the present invention. Hemodilution with the compositions is performed in a manner conventional in the art, for example, as described in Messmer et al., *Prog. Surg.*, 13, 208–245 (1974). The present invention also contemplates that cyclic GMP generating compounds may simply be infused peri-hemodilution with a hemoglobin product. The methods of treatment of the invention are particularly useful in treating humans.

The contents of this specification are submitted as sufficient objective factual evidence that the invention claimed is not prima facia obvious under 35 U.S.C § 103 and that the invention claimed could not have been expected to be achieved by one of ordinary skill since the art was not of public record at the time the invention was made.

The prior art only demonstrated that hemodilution, i.e. substitution of red cell mass, with hemoglobin failed to provide increased cardiac output or oxygen delivery. Exactly how this happens or the expected methods of reversing this result were not known in the art at the time the invention was made. The prior art did not know that hemoglobin-based material selectively inhibits vasomotor activity in arteries that is different from the inhibited vasomotor activity by hemoglobin-based material in veins. It was not known by anyone skilled in the art, except the applicant, that coupling of hemoglobin and nitric oxide groups (nitrovasodilators) and particularly hemoglobin and NO from Na nitroprusside (SNP) would increase cardiac output. The prior art knew for over 100 years that hemoglobin-based material binds nitric oxide, that hemoglobin-based material is a potential biocolloid, and that SNP is a vasodilator, however, the invention claimed was not prima facia obvious and was pure luck. In fact, the applicant expected that the NO donor used from SNP would not work since, in control animals or patients, SNP dilates arteries and veins equally, decreases blood pressure and rarely increases cardiac output unless heart rate increases. Therefore, the unexpected result was that SNP can not dilate veins in the presence of hemoglobin-based material thereby not affecting preload. This result discovered that hemoglobin does not effect arteries and veins equally. Blood pressure was also little affected, another unexpected result. Because of these unexpected results, stroke volume (i.e. cardiac output) was allowed to increase inversely proportional to the reduced viscosity component of afterload.

This invention will not work with every NO donor. For example, nitroglycerin and cyclic GMP analogues, in their present commercial formulation, will dilate both veins and arteries, with or without hemoglobin-hemodilution. There is no increase in cardiac output because both preload and afterload are reduced. This is further evidence that hemoglobin-based material affects arteries and veins by different mechanisms and that one skilled in the art could not expect this result, or, one skilled in the art could not expect that the invention claimed could be achieved.

The invention uses a series of related dihydropyridines to selectively provide various time-controlled oxygen deliveries. These compounds are classically slow channel calcium antagonists that preferentially dilate arteries to lower blood pressure over specific time periods. In the absence of hemoglobin products, the dihydropyridine compounds generate cyclic GMP with increases of 20–70% from baseline levels. In the presence of hemoglobin products, the dihydropyridine compounds provide hemodynamics similar to those achieved with SNP, i.e. little effect on blood pressure and preload but appropriate reversal of hemoglobin antagonism in arteries. The fact that these compounds are unexpectedly similar to SNP in dilating arteries preferentially over veins suggests that hemoglobin-based material probably antagonizes the guanylate cyclase enzyme rather than scavenging NO directly or antagonizing the NO synthase enzyme. Oxygen delivery, therefore, is similar to SNP but has the additional advantage of being time-controlled.

The invention uses cyclic GMP generating compounds as the principle means of increasing oxygen delivery with any hemoglobin-based material. The evidence from the SNP and dihydropyridine studies and other studies of record presented in this communication clearly demonstrate that hemoglobin-based material inactivates or antagonizes more than one NO→cyclic GMP mechanism, i.e. effects on NO→cGMP mechanisms in arteries are not expected to be physiologically equivalent to those in veins. Furthermore, the reversal of hemoglobin inactivation or antagonism is dependent on more than one NO→cyclic GMP mechanism, i.e. reversal of NO→cGMP antagonism in arteries is not expected to be physiologically equivalent to that in veins. Therefore, the invention selectively acts on those NO→cGMP mechanisms to decrease afterload while having little effect on NO→cGMP mechanisms that control preload.

In summary, the specification is submitted as sufficient objective factual evidence, with unexpected results, that the invention claimed is not prima facia obvious under 35 U.S.C § 103 and that the invention claimed could not have been expected to be achieved by one of ordinary skill in the art since the art or knowledge of the selective vasoactive mechanisms of hemoglobin-based material and claimed compounds required for control of these mechanisms was not known at the time the invention was made.

DETAILED DESCRIPTION

Figure 1A:
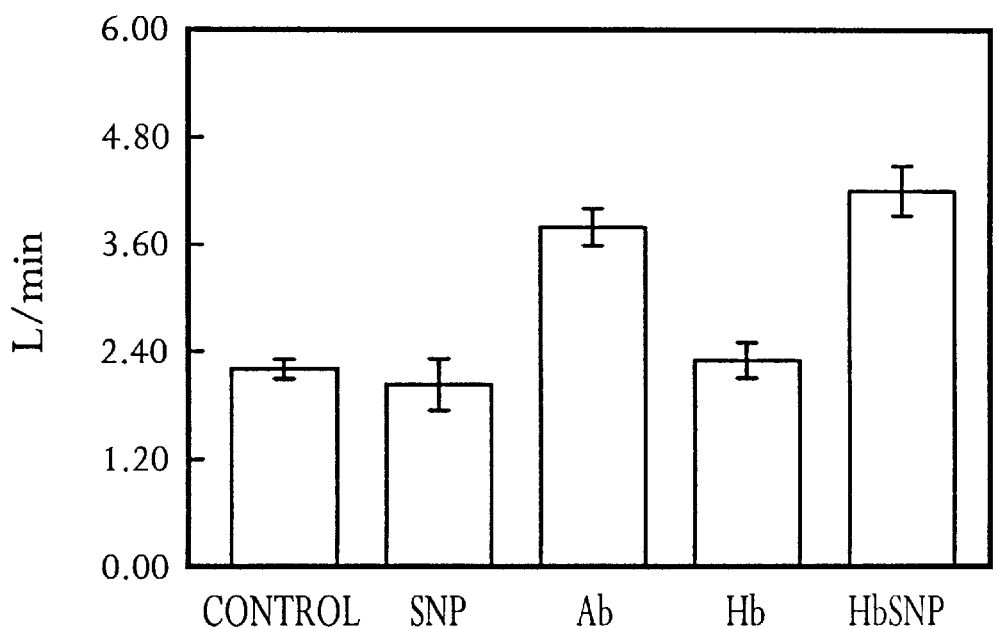
FIG. 1A is bar graph representing the cardiac output (L/minute) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.
Figure 1B:
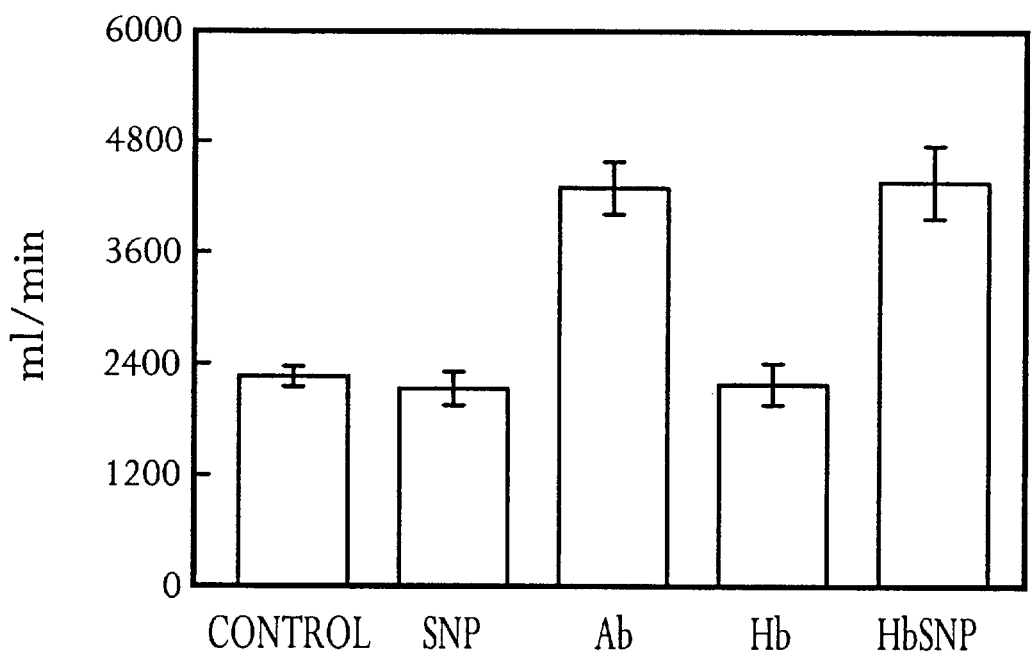
FIG. 1B is a bar graph representing the sum of regional blood flows (ml/minute) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.
Figure 1C:
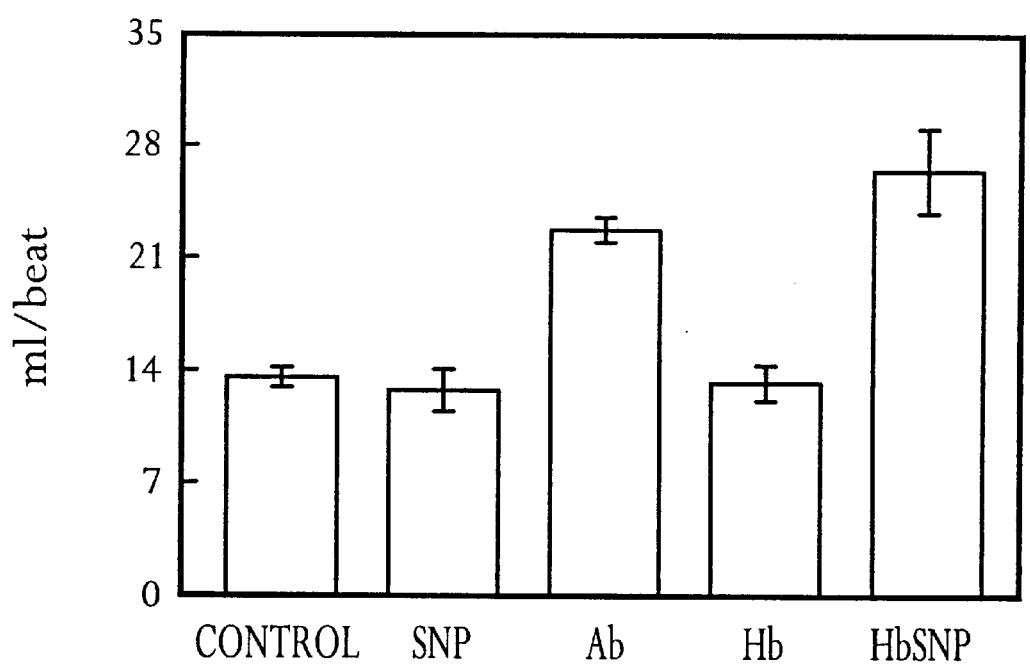
FIG. 1C is a bar graph representing the stroke volume (ml/beat) (computed from cardiac output) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.
Figure 1D:
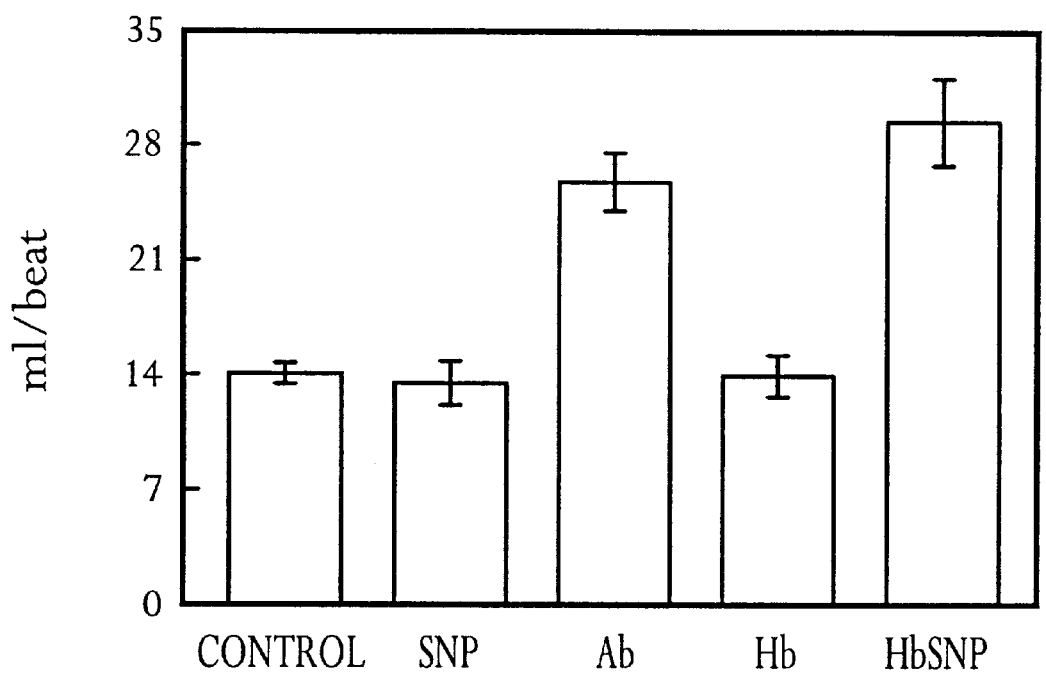
FIG. 1D is a bar graph representing the stroke volume (ml/beat) (computed from sum of regional blood flows) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.
Figure 2A:
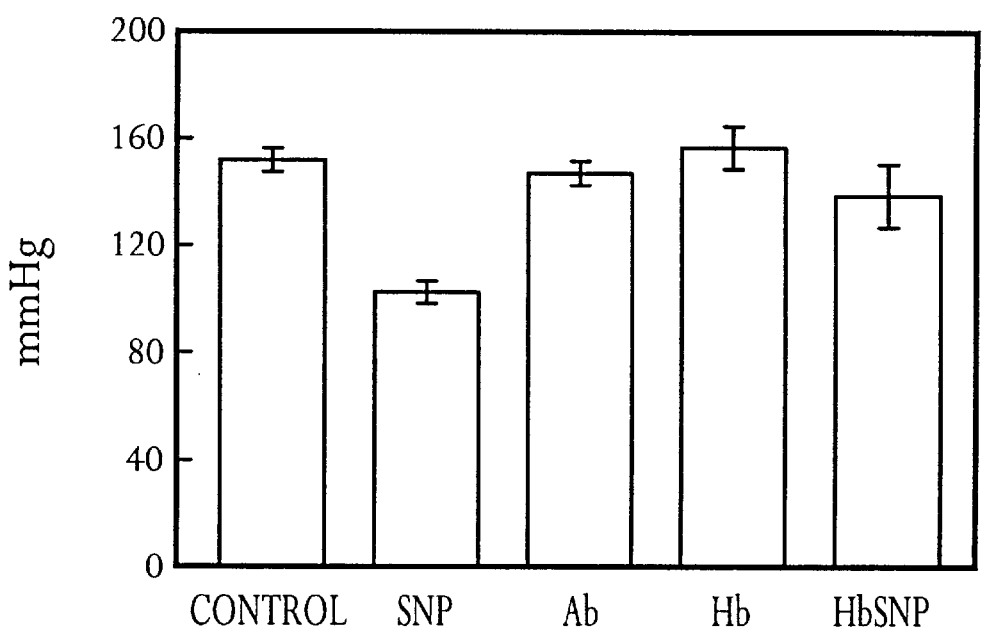
FIG. 2A is a bar graph representing the systolic aortic pressure (mm Hg) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.
Figure 2B:
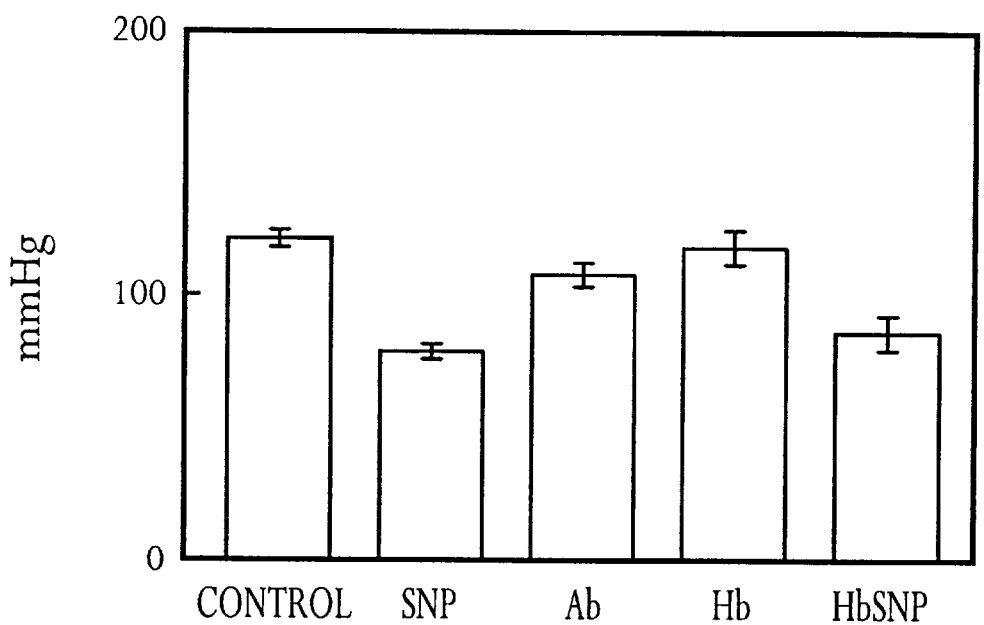
FIG. 2B is a bar graph representing the diastolic aortic pressure (mm Hg) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.
Figure 2C:
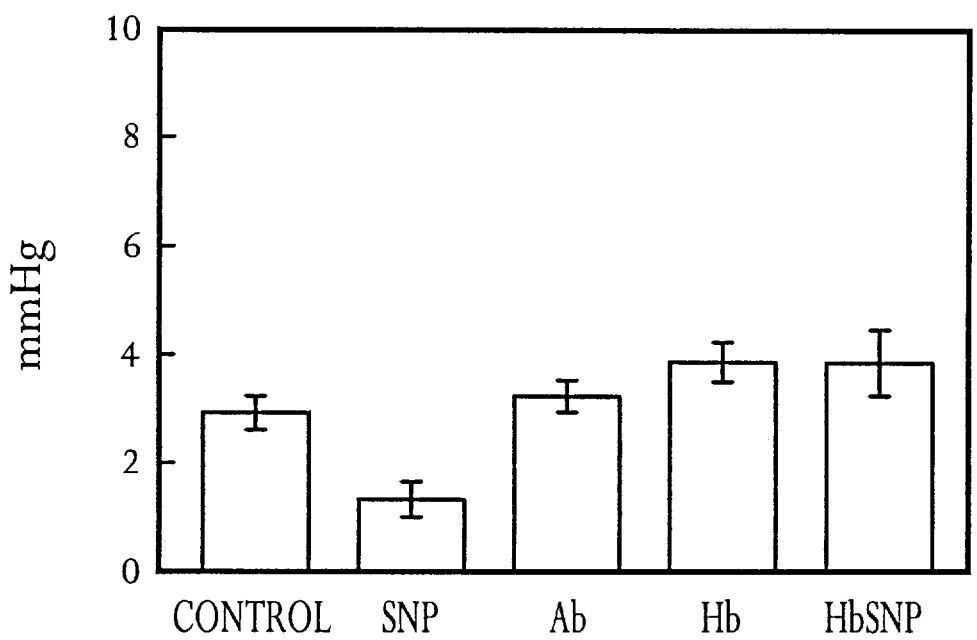
FIG. 2C is a bar graph representing the right atrial pressure (mm Hg) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.
Figure 2D:
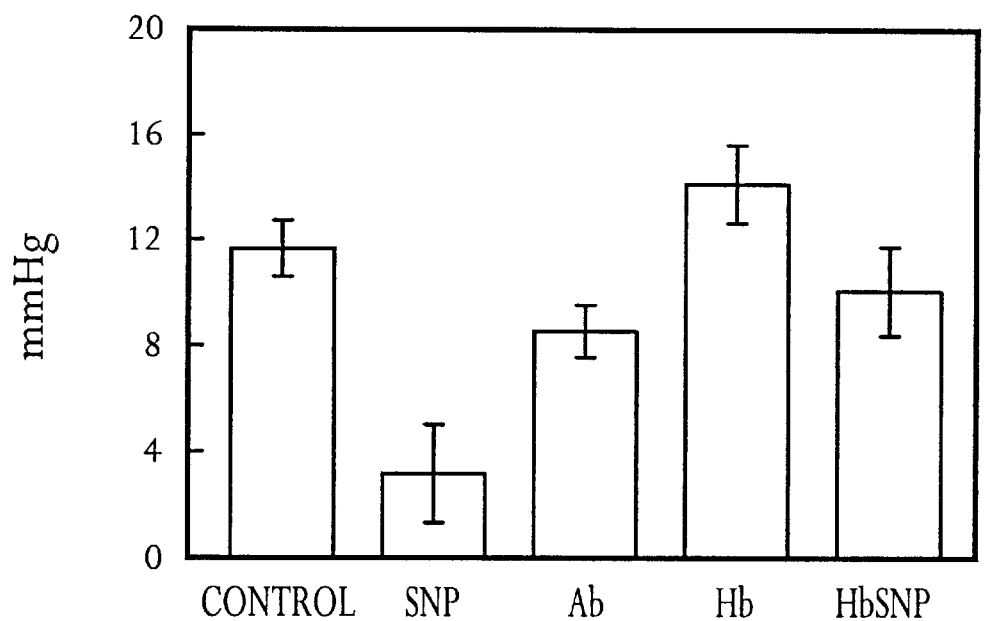
FIG. 2D is a bar graph representing the left ventricular end-diastolic pressure (mm Hg) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.

The following examples illustrate practice of the invention in treating mammals with combinations of hemoglobin and cyclic GMP-generating compounds. The examples are not to be construed as limiting the invention.

EXAMPLE I

As discussed previously, hemodilution with hemoglobin produces a hemodynamic profile of no increase in cardiac output, a profile which is uncharacteristic for hemodilution. Hemodilution with combinations of hemoglobin and cyclic GMP-generating compounds, on the other hand, augments cardiac output as is illustrated below.

Twelve dogs were hemodiluted with a hemoglobin product according to the present invention either in the presence or absence of excess intravascular nitric oxide provided by sodium nitroprusside (SNP) infusion as the cyclic GMP generating compound. Hemodilution with albumin of twelve dogs also either in the presence or absence of excess intravascular nitric oxide was performed as a control. Human albumin in normal saline was purchased as Albuminar-25 (25 mg %) from Armour Pharmaceutical Company (Kankakee, Ill.). The systemic and regional hemodynamic responses of the twenty-four dogs were then measured. SNP was chosen as a nitric oxide-associated compound because, unlike other nitrovasodilators, it is acts equally on both arteries and veins, it does not generate superoxide and it has no apparent requirement for cofactors or oxidative processes. See, Van Zwieten, *Handbook of Hypertension: Pharmacology of Antihypertensive Drugs*, 3, 308–330 (1984). The study was approved by the Loyola University Animal Care and Use Committee and performed in accordance with the National Research Council's Guide for the Use of Laboratory Animals.

Hemoglobin Preparation

Canine hemoglobin (10 gm %) was purified as described in the parent application Ser. No. 07/849,610 filed on Mar. 11, 1992 and subsequently published by Rooney et al., *Anesthesiology*, 79, 60–72 (1993). A 10 gm % solution of hemoglobin is optimal for use as a resuscitative fluid or blood plasma expander because the 10 gm % concentration corresponds to the mass of red cells in blood (i.e., a hematocrit of 30 vol %) which is optimal for whole body oxygen delivery (calculated from arterial blood oxygen content×cardiac output). A 10 gm % solution of hemoglobin is oncotically active, has a lower viscosity than whole blood, and binds 1.34 cc of oxygen per gram of hemoglobin at ambient oxygen pressures.

Various properties of the hemoglobin product are set out below in Table 1.

TABLE 1

| PROPERTY | VALUE |
| --- | --- |
| Total Hb concentration | 10 gm % |
| % methemoglobin | < 1% |
| % carboxyhemoglobin | < 0.5% |
| % sulfhydrylhemoglobin | Unknown |
| % nitrosylhemoglobin | Unknown |
| Colloid osmotic pressure | 40 mm Hg |
| Viscosity | ≈ 2.0 cp |
| $P_{50}$ | 24 mm Hg (pH 7.4) |
| Bohr coefficient | 0.54 (pH 7.2–7.4) |
| Hill plot | Normal |
| Haldane effect | Normal |
| Davenport diagram | Normal |
| Oxygen content | 13.5 vol % |
| Oxygen capacity | 13.5 vol % |
| pH | 6.9 |
| $PCO_2$ | 15 mm Hg |
| $PO_2$ | 200 mm Hg |
| Na | 150 mmol/L |
| K | 3.4 mmol/L |
| $Ca^+$ | 1.2 mmol/L |
| Osmolality | 310 mOsmol/kg |

TABLE 1-continued

| PROPERTY | VALUE |
| --- | --- |
| Dimers | Unknown |
| Monomer | Unknown |
| Free heme | Unknown |
| Free iron | Unknown |
| Trace metals | Unknown |

Results not presented in Table 1 are that methemoglobin levels were stable at ±0.4% for two weeks at 4° C., and that while hemoglobin dimers and monomers and free heme were not measured, in vitro studies have shown that for hemoglobin concentrations of above about 1 to 2 gm % there is no detectable dissociation of hemoglobin tetramers [see Fanelli et al., *Adv. Protein Chem.*, 19, 96–117 (1964)].

The hemoglobin product was also tested in vivo on dogs for common adverse effects of therapeutic products which are administered intravascularly. The hemodilution protocol used and the physiologic tests performed are standard in the art and were similar to that described in Rabiner et al., *J. Exp. Med.*, 86, 455–463 (1967); Sunder-Plassmann et al., supra; and Crystal et al., *Anesth. Analg.*, 67, 211–218 (1988) Briefly, the hemoglobin product was infused into a venous access of an anesthetized dog with simultaneous withdrawal of arterial blood on a one-to-one basis at about 25 ml/minute until hematocrit was 50% of baseline (about 20 vol %). Tests for pyrogenic effects, hypotensive effects, arrhythmia, inotropic effects, bradycardia, tachycardia, hypovolemia, dysoria, and coagulopathy were all negative.

Surgical Preparation

Twenty-four conditioned, heartworm-free male mongrel dogs (20 to 30 kg) were anesthetized with sodium pentobarbital (30 mg/kg i.v.) followed by an i.v. maintenance dose of 4 mg/kg/hour. After intubation of the trachea with a cuffed endotracheal tube, the dog was mechanically ventilated (Siemens 900D Servoventilator) with 100% oxygen, tidal volumes of 10 to 12 ml/kg and respiration at a rate to achieve normocarbia. These settings were not changed throughout the study. Sodium bicarbonate was not administered. The body temperature of the dog was maintained at 39 C. with water-circulated heating pads.

The dog was placed supine and a polyethylene catheter (PE 200) was inserted into the thoracic aorta via the left femoral artery for measurement of blood pressure. Two small-bore (PE 90) heparin-filled catheters of different lengths were placed in the abdominal aorta via the right femoral artery to collect reference blood samples containing radioactive microspheres for measurement of regional blood flow. Wide-bore (PE 240) catheters were placed in the right femoral vein and in the right carotid artery, for isovolemic exchange transfusion and for the administration of intravenous fluids and collection of arterial blood samples. A 5 french thermodilution catheter was advanced into the pulmonary artery via the right external jugular vein for measurement of cardiac output and right atrial pressure. A Foley catheter was inserted into the bladder for urine collection.

Under fluoroscopy, a 5 french volume-conductance catheter (Mansfield Webster) was inserted via the left carotid artery across the aortic valve to the apex of the left ventricle to measure instantaneous volume. An 8/10 french Fogarty venous thrombectomy catheter was placed via the left femoral vein into the inferior vena cava just above the diaphragm to produce occlusive-unloading of the left ventricle over several cardiac cycles (20 seconds) during collection of pressure-volume data.

The animal was then placed on its right side and paralyzed with doxacurium (0.05 mg/kg) to perform a left thoracotomy in the fourth intercostal space. The exposed lung was retracted with gauze. Five cm $H_2O$ positive end-expiratory pressure was instituted to prevent atelectasis. A small incision was made in the pericardium near the left atrial appendage. The appendage was protracted and a PE 90 catheter, for microsphere injection, inserted into the ventricle via pressure verification and then pulled back into the atrium. A 3 french micromanometer-tipped pressure catheter (Millar) was then inserted via the appendage into the left ventricle for pressure recording. Both catheters were secured with a ligature around the appendage and distally taped to the animal. The exposed thoracic surface was covered with plastic film to prevent evaporation.

Measurements and Calculations

Continuous measurements of heart rate (HR), pulsatile aortic pressure, mean aortic pressure (MAP), left ventricular peak pressure (LVPP), rate-of-change of LVPP (dP/dt), LV end diastolic pressure (LVEDP), LV volume, and right atrial pressure (RAP) were recorded on an analog thermal array recorder (Gould Model TA4000) and stored on a computerized data acquisition system (Halcom, Inc.) Cardiac output (CO) was measured in triplicate using a Spectramed Hemoprol computer. Systemic vascular resistance (SVR) was calculated from (MAP−RAP)÷CO. Systemic vascular hindrance (SVH) was calculated from SVR÷η, where η is the apparent viscosity of blood in centipoise (cp). At high flow rates (shear rates $\approx 200$ $s^{-1}$) assumed in the aorta, η is 4.0 cp for hematocrit (Hct) of 40 vol % and 2.1 cp for Hct of 20 vol %. Stroke volume was derived from CO÷HR. LV stroke work (LVSW) was calculated from (systolic AoP−LVEDP)×SV×0.0136.

Blood pH, $PCO_2$, $PO_2$ and $Na^+$, $K^+$ and $Ca^{++}$ concentrations were measured with a Nova Stat Profile 1 analyzer (Waltham, Mass.). Plasma colloid osmotic pressure (COP) was determined before and after hemodilution with a Wescor 4400 Colloid Osmometer (Logan, Utah). The COP of 8% albumin was 39.3±0.9 mm Hg. The COP of 10% hemoglobin was 40.8±1.0 mm Hg. Hematocrit was determined volumetrically. Hemoglobin (gm %), methemoglobin (%) and percent oxygen saturation were measured with an Instrumentation Laboratories 482 CO-Oximeter (Lexington, Mass.). Hemoglobin oxygen content was measured with the co-oximeter and added to the dissolved oxygen (0.003×$PO_2$) to give total blood oxygen content (vol %).

Whole body oxygen extraction ratio ($O_2$ extr, %) was calculated from arteria-mixed venous oxygen content difference C(a-v)$O_2$ divided by the arterial oxygen content (Ca$O_2$). Whole body oxygen consumption (WBV$O_2$) in ml/minute was determined using the Fick equation, WBV$O_2$=CO×C(a-V)$O_2$. Oxygen delivery (D$O_2$) in ml/minute was calculated from Ca$O_2$×CO.

Catecholamines (pg/ml) were measured in arterial plasma using high-performance liquid chromatography with electrochemical detection (RAS 400 Liquid Chromatograph (West Lafayette, Ind.). Arterial plasma lactate concentrations (meq/L) were measured enzymatically with an Easy ST analyzer (E. Merck, Gibbstown, N.J.). Blood cyanide levels (mg/L) were measured spectrophotometrically by SmithKline Beecham Clinical Laboratories (Schaumburg, Ill.).

Total blood volume was computed from plasma volume (indicator dilution of iodinated $I^{125}$-albumin, Mallinckrodt Medical, Inc., St. Louis, Mo.) and whole body hematocrit.

Regional Blood Flows and Distribution of Cardiac Output

Regional blood flows (ml/minute/100 g tissue) were measured with the reference isotope technique using 15μ microspheres as described in detail in Crystal et al., supra. Briefly, prior to injection, microspheres labeled with $Sc^{46}$, $Sr^{85}$, $Sn^{113}$ or $Ce^{141}$ were vortexed and sonicated. Approximately 30 microcuries (1×$10^6$ microspheres) were injected into the left atrium of a dog. Beginning with each microsphere injection, duplicate reference blood samples were collected at a constant rate (6 ml $min^{-1}$) for 3 minutes from the femoral PE 90 catheters. Radioactivity of the duplicate samples differed by less than 10%, indicating adequate mixing of the microspheres in the left ventricular output. To maintain isovolemic conditions during reference sampling, a 5% albumin solution was infused simultaneously.

After the final injection of microspheres, the heart was stopped by intravenous injection of potassium chloride. Skin and bone (rib) were sampled from a shaved area distal to the thoracotomy. Skeletal muscle samples were taken from the hindlimb, back, forelimb and head. The GI tract was excised from the esophageal sphincter to the anus. All mesentery and omentum were trimmed. The stomach was separated from the tract. These and all other organs were weighed. Multiple samples were taken from each organ and transferred to a tared counting tube.

The tissue and reference samples were weighed and analyzed for radioactivity with a gamma scintillation counter equipped with a multichannel analyzer (Packard Instrument, Downers Grove, Ill.). Isotope separation was accomplished by standard techniques of gamma spectroscopy. Values for organ blood flows ($BF_{organ}$) in ml $min^{-1}$ were calculated from the equation $BF_{organ}$=ABF× (MC÷AC)×organ weight (g), where ABF is the rate of arterial reference sampling (ml/minute), MC is the microsphere radioactivity (counts $min^{-1}$ $g^{-1}$) in the tissue samples, and AC is the total microsphere radioactivity (counts/minute) in the arterial reference samples. The fractional distribution of cardiac output to each organ was computed from $BF_{organ}$=Σ$BF_{organ}$, where Σ$BF_{organ}$ is the sum of all organ flows. Skeletal muscle, skin and bone weights were calculated as 40%, 9% and 8% of body weight, respectively.

Left Ventricular End-Systolic Elastance ($E_{es}$)

Left ventricular contractility was determined from end-systolic elastance (Ees) using pressure-volume relationships according to the methods of Kass et al., *Circulation*, 79, 167–178 (1989). Briefly, a catheter with 11 electrodes spaced 1 cm from its distal end was positioned in the ventricle so that its tip was at the apex (verified with fluoroscopy). A weak electrical field (20 KHz, 0.03 mA RMS current) was generated through the LV cavity from the electrodes at the apex and at the aortic valve. Conductances measured between pairs of electrodes within the field provided a volume conductance measurement that includes the actual ventricular volume plus an offset volume dependent on structures surrounding the ventricular cavity (LV tissue, RV tissue and blood, and juxtapericardial tissue). The offset volumes were ignored because only relative volume changes, not absolute volume measurements, were considered in the final analysis.

The volume signals were processed by a Leycom Sigma 5 signal conditioner (Stitching, Holland). An inferior vena caval occlusion varied preload to the heart, during which the first 10–15 cardiac cycles (or pressure-volume loops) were collected. As preload decreased the area of each loop decreased. An algorithm was then used to find the end-systolic pressure-volume point of each loop. A linear regression line through each point determined an equation, the end-systolic pressure-volume relationship (ESPVR). The slope of the ESPVR, called the end-systolic elastance ($E_{es}$), is a load independent measure of global left ventricular contractility. Increases and decreases in $E_{es}$ correspond to increases and decreased in contractility, respectively. Limitations to this technique: the conductance offset volume could potentially change from cardiac cycle to cardiac cycle during an occlusion thus skewing the ESPVR in one direction or another. To test for this error we made slow (20 second) and fast (5 second) occlusions during either end-inspiratory or end-expiratory pauses. We found no difference in the measured $E_{es}$ values determined in this manner.

Experimental Protocol

Upon arrival in the laboratory, typically all dogs had hematocrits of 45 vol % or greater and filling pressures (LVEDP) of 5 mm Hg or less. Following cannulation all animals were hydrated with 5 mg % albumin to increase filling pressure (LVEDP) above 5 mm Hg and to bring hematocrit to near 40 vol %. Twelve dogs underwent isovolemic exchange of blood for 10 gm % hemoglobin to hematocrit 50% of baseline. Twelve more dogs were exchanged transfused with 8 gm % albumin in order to compare effects of hemodilution with hemoglobin to those of hemodilution with an inert colloid having a comparable molecular weight (both hemoglobin and albumin have molecular weights of about 65,000). The colloid pressure of 10 gm % hemoglobin and 8 gm % albumin (both about 40 Torr) is about twice that of dog plasma and after in vivo dilution would be expected to sustain plasma volumes at baseline values or greater. The smaller weight fraction of albumin needed to obtain a colloid pressure similar to hemoglobin is due to differences in surface charge, molecular shape, intermolecular association and hydration properties of the two colloids.

Hemodilution was produced by a simultaneous isovolemic exchange of blood for hemoglobin or albumin (rate of 20 ml/minute, about 45 ml/kg). Following the exchange all measurements and samples were obtained within 30 minutes. SNP was then infused in five of the dogs hemodiluted with albumin and in ten of the dogs hemodiluted with hemoglobin. The end-point for SNP infusion was to obtain a decrease in mean aortic pressure (MAP) of at least about 10 mm Hg but not more than about 50 mm Hg. The total dose of SNP varied (0.75–1.5 mg/kg) depending on the time (15–25 minutes) to reach the endpoint, record hemodynamic data and to draw reference microsphere and other blood samples. Blood volume measurements were made after SNP infusion was discontinued.

Effects of Infusion of SNP Alone

A total of eight dogs, randomly selected from either the hemoglobin or albumin group, were given SNP (2.3±0.4 μg $kg^{-1}$ $minute^{-1}$ i.v.) before hemodilution with hemoglobin or albumin in order to establish the hemodynamic effects of SNP on these dogs. Baseline measurements were made, then SNP was infused to decrease mean aortic pressure (MAP) by 40% to about 90 mm Hg. Once MAP stabilized (≈5–10 min), hemodynamic measurements, blood gases and other samples were obtained.

Cardiac output and stoke volume, computed via thermodilution or via the sum of regional blood flows, are shown in FIGS. 1A–1D. There was no significant difference in values obtained by the two computation methods.

Moderate hypotensive doses of SNP (2.3±0.3 μg $kg^{-1}$ $min^{-1}$) had no effect on cardiac output or stroke volume (See FIGS. 3A–3B) but systolic, diastolic and mean aortic pressures were decreased about 34%. See Table 2 below wherein "n" values represent the number of dogs treated with SNP alone (SNP), albumin alone (AbHD), hemoglobin alone (HbHD) or hemoglobin in combination with SNP (HbHD+SNP).

Left ventricular dP/dtmax decreased 44% as peak pressure decreased 33%, however LV elastance (contractility) was not changed from control values (See Table 2). Systemic vascular resistance and vascular hindrance both decreased approximately 31% (FIGS. 3A–3B), while right atrial pressure and left ventricular end-diastolic pressure decreased 55% and 73% respectively (FIGS. 2A–2D).

The foregoing results indicate that the decrease in blood pressure was due entirely to reductions in afterload and preload caused by decreases in arteriolar and venous tone, respectively. Left ventricular stroke work decreased 37%. Heart rate was not affected by these doses of SNP.

Blood parameters (arterial pH, $PCO_2$, $PO_2$, hemoglobin, blood volume, etc.) and whole body oxygenation were not significantly different from control values. See Table 2, and Tables 3 and 4 below wherein "n" values represent the number of dogs treated with SNP alone (SNP), albumin alone (AbHD), hemoglobin alone (HbHD) or hemoglobin in combination with SNP (HbHD+SNP).

Regional blood flows and the fractional distribution of cardiac output to various organs were not affected by the moderate hypotensive doses of SNP. (See FIGS. 4 and 5)

TABLE 2

| Variable | Control n = 24 | SNP n = 8 | AbHD n = 12 | HbHD n = 12 | HbHD + SNP n = 10 |
|---|---|---|---|---|---|
| MAP (mm Hg) | 134 ± 3 | 85 ± 3 | 122 ± 4 | 136 ± 6 | 110 ± 6 |
| LVPP (mm Hg) | 153 ± 3 | 104 ± 8 | 150 ± 3 | 154 ± 6 | 139 ± 5 |
| LV dP/dtmax (mm Hg/sec) | 1669 ± 88 | 938 ± 118 | 1753 ± 137 | 1713 ± 76 | 1887 ± 171 |
| LV Elastance (mm Hg ml) | 4.78 ± 0.27 | 4.26 ± 0.73 | 5.26 ± 0.35 | 4.91 ± 0.58 | 4.24 ± 0.55 |
| LVSW (g m/beat) | 27.9 ± 1.5 | 17.7 ± 1.5 | 45.3 ± 3.5 | 29.2 ± 3.4 | 47.8 ± 4.71 |
| heart rate (beats/min) | 160 ± 4 | 161 ± 9 | 167 ± 6 | 153 ± 5 | 153 ± 7 |
| Blood Volume (ml) | 1885 ± 81 | 1834 ± 75 | 1856 ± 102 | 1892 ± 125 | 1805 ± 118 |

TABLE 3

| Parameter | Control n = 24 | SNP n = 8 | AbHD n = 12 | HbHD n = 12 | HbHD + SNP n = 10 |
|---|---|---|---|---|---|
| pH | 7.39 ± 0.01 | 7.33 ± 0.02 | 7.35 ± 0.01 | 7.38 ± 0.01 | 7.36 ± 0.02 |
| $PCO_2$ (mm Hg) | 35 ± 1 | 33 ± 1 | 37 ± 2 | 34 ± 2 | 35 ± 2 |
| $PO_2$ (mm Hg) | 390 ± 21 | 301 ± 36 | 439 ± 33 | 411 ± 31 | 424 ± 33 |
| Hematocrit (vol %) | 42 ± 1 | 40 ± 1 | 20 ± 1 | 21 ± 1 | 20 ± 1 |
| $Na^+$ (mmol/L) | 151 ± 1 | 152 ± 1 | 152 ± 1 | 152 ± 1 | 152 ± 1 |
| $K^+$ (mmol/L) | 3.4 ± 0.1 | 3.5 ± 0.2 | 3.3 ± 0.1 | 3.7 ± 0.2 | 3.6 ± 0.1 |
| $C^{++}$ (mmol/L) | 1.27 ± 0.02 | 1.22 ± 0.03 | 1.17 ± 0.03 | 1.15 ± 0.05 | 1.12 ± 0.08 |
| Total Hb (g/100 ml) | 14.7 ± 0.3 | 14.0 ± 0.6 | 7.1 ± 0.2 | 11.5 ± 0.5 | 10.0 ± 0.1 |
| Total MetHb (%) | 0.8 ± 0.04 | 0.5 ± 0.09 | 0.8 ± 0.06 | 0.8 ± 0.07 | 1.0 ± 0.09 |
| Plasma Hb (g/100 ml) | — | — | — | 4.6 ± 0.2 | 3.4 ± 0.1 |
| Plasma MetHb (%) | — | — | — | 1.5 ± 0.16 | 1.5 ± 0.17 |
| Plasma COP (mm Hg) | 18.7 ± 0.6 | 18.9 ± 0.6 | 22.5 ± 0.7 | 22.8 ± 0.8 | 20.9 ± 0.6 |

TABLE 4

| Parameter | Control n = 24 | SNP n = 8 | AbHD n = 12 | HbHD n = 12 | HbHD + SNP n = 10 |
|---|---|---|---|---|---|
| $CaO_2$ (ml/100 ml) | 19.7 ± 0.4 | 18.8 ± 0.5 | 10.0 ± 0.2 | 14.9 ± 0.4 | 13.2 ± 0.3 |
| $CvO_2$ (ml/100 ml) | 14.2 ± 0.6 | 13.0 ± 0.7 | 6.8 ± 0.5 | 8.8 ± 0.6 | 9.7 ± 0.7 |
| $C(a-v)O_2$ (ml/100 ml) | 5.1 ± 0.3 | 5.3 ± 0.3 | 2.7 ± 0.4 | 6.1 ± 0.4 | 3.3 ± 0.3 |
| $O_2$ extr (%) | 27 ± 3 | 30 ± 4 | 30 ± 2 | 45 ± 3 | 27 ± 4 |
| $DO_2$ (ml/min) | 434 ± 18 | 404 ± 35 | 418 ± 25 | 302 ± 22 | 518 ± 38 |
| $WBVO_2$ (ml/min) | 122 ± 8 | 119 ± 15 | 126 ± 10 | 125 ± 11 | 131 ± 14 |

In general, the systemic and regional effects of SNP infusion before hemodilution were in agreement with other studies. See Hoka et al., *Anesthesiology*, 66, 647–652 (1987); Wang et al., *Anesthesiology*, 46, 40–48 (1977); Fan et al., *Anesthesiology*, 53, 113–120 (1980); Gelman et al., *Anesthesiology*, 49, 182–187 (1978); and Kien et al., *Anesth. Analg.*, 66, 103–110 (1987).

In summary, intravenous infusion of 2.3±0.4 $\mu$g kg$^{-1}$ min$^{-1}$ of SNP before hemodilution decreased MAP about 37% with no change in heart rate or cardiac output. There was no significant effect of SNP treatment on pre-hemodilution baseline data, i.e., dogs treated with SNP and dogs not treated with SNP had similar hemodynamic profiles before hemodilution.

Effects of Hemodilution with Albumin

Figure 3A:
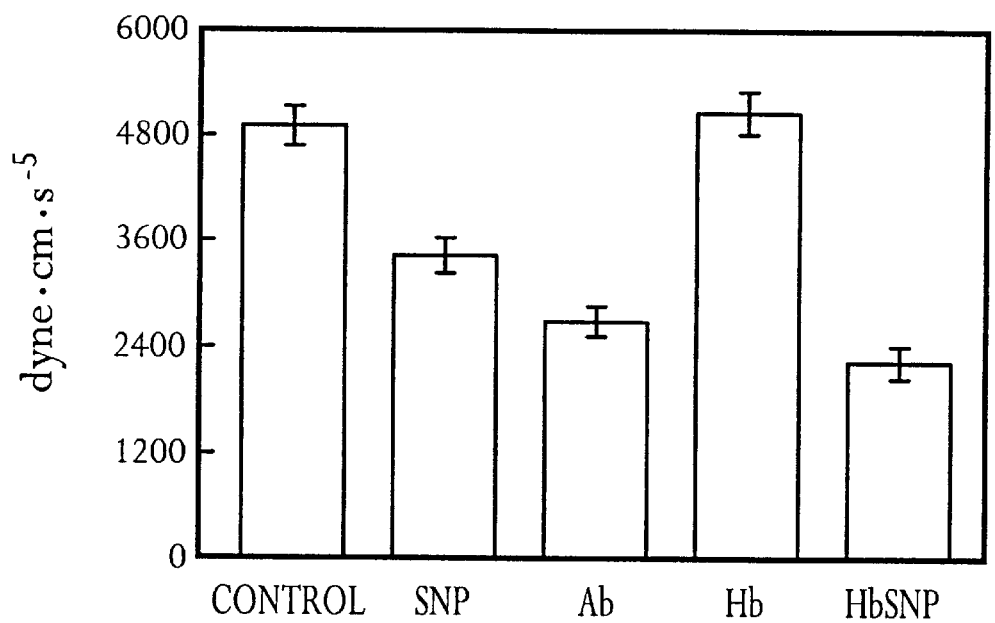
FIG. 3A is a bar graph representing the systemic vascular resistance (dyne·cm·s$^{-5}$) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.
Figure 3B:
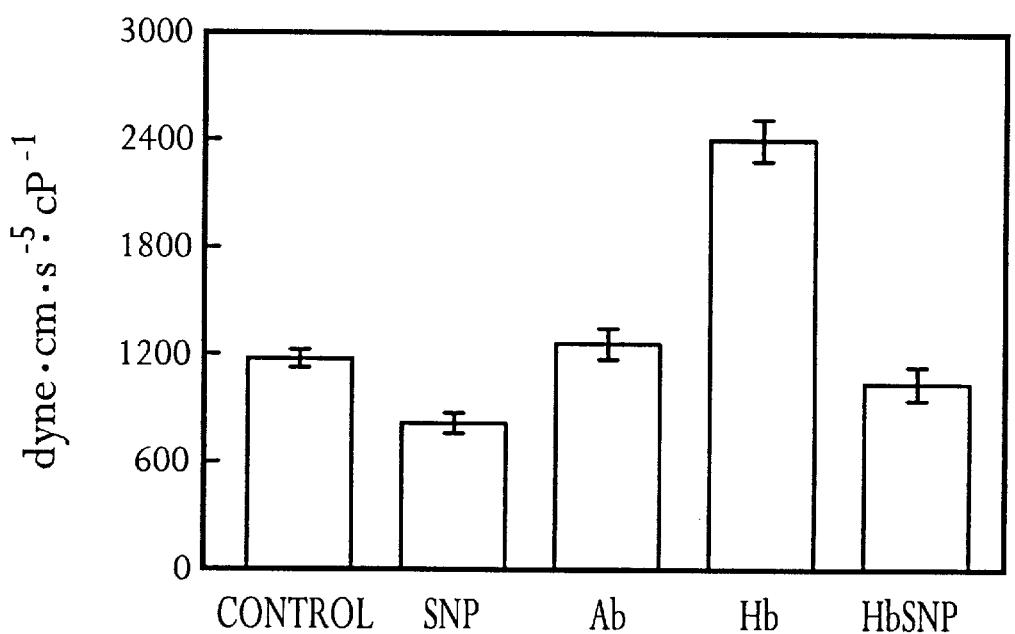
FIG. 3B is a bar graph representing the systemic vascular hindrance (dyne·cm·s$^{-5}$·cP$^{-1}$) of control, sodium nitroprusside-treated (SNP), albumin-hemodiluted (AB), hemoglobin-hemodiluted (Hb), and hemoglobin/sodium nitroprusside-hemodiluted (HbSNP) mongrel dogs.

Hemodilution with albumin to a hematocrit 50% of control (20±1 vol %) caused cardiac output to increase to approximately 177% of control as is shown in FIGS. 1A–1D. Proportional increases occurred in stroke volume as heart rate did not change. Left ventricular stroke work increased markedly. (See Table 2) Hemodilution reduced systemic vascular resistance to about 54% of control but did not change systemic vascular hindrance (FIGS. 3A–3B). Mean aortic, right atrial and LV end-diastolic pressures were not changed. Thus the reduction in systemic vascular resistance was directly proportional to the apparent decrease in viscosity (assumed 50% of control) rather than to changes in arteriolar tone. Stroke volume and cardiac output increased because the viscosity component of afterload was reduced allowing more complete emptying of the ventricle.

Hemodilution with albumin caused an approximate 50% reduction in hemoglobin concentration (14.7±0.3 to 7.0±0.2 g/100 ml) and arterial oxygen content (19.7±0.4 to 10.0±0.2 ml/100 ml) (See Tables 3 and 4). The arterial-mixed venous oxygen content difference decreased 47% while oxygen extraction ratio was unchanged. Total body oxygen delivery and whole body oxygen consumption were not changed from control values. Arterial blood gases, electrolytes and plasma catecholamines were within the control range (See Table 3 and Table 5 below). Hemodilution with hyperoncotic 8 gm % albumin caused plasma colloid osmotic pressure to increase 20% yet there was no significant increase in blood volume. (See Tables 2 and 3)

Figure 4A:
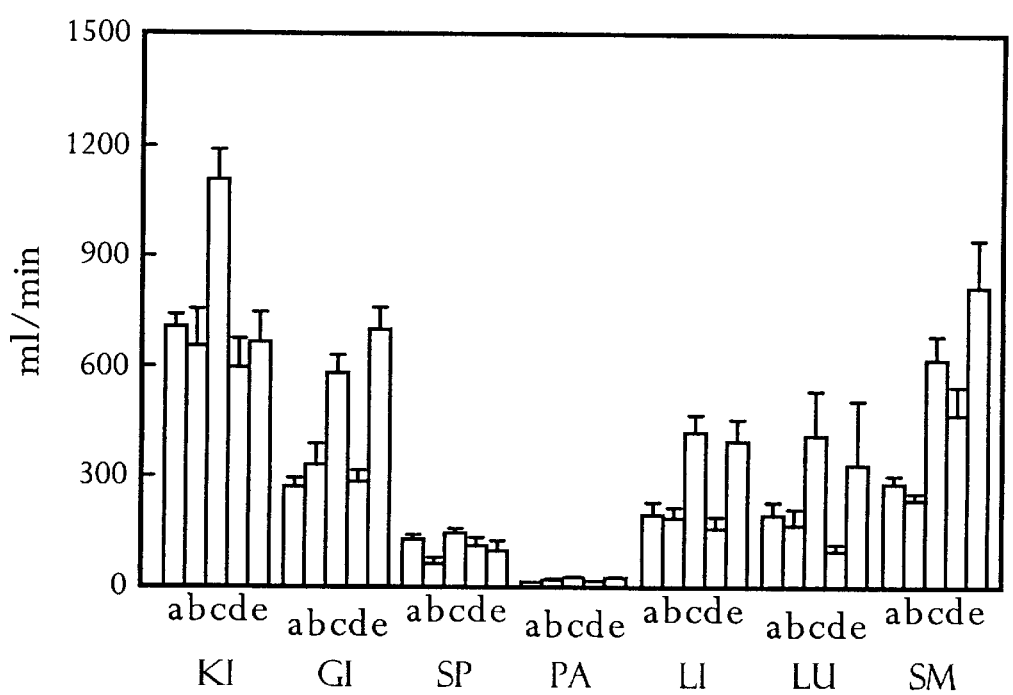
FIG. 4A is a bar graph representing the regional blood flows (ml/minute) in the kidney (KI), gastrointestinal tract (GI), spleen (SP), pancreas (PA), liver/hepatic arteries (LI), lung/bronchial arteries (LU) and skeletal muscle (SM) of control (a), sodium nitroprusside-treated (b), albumin-hemodiluted (c), hemoglobin-hemodiluted (d), and hemoglobin/sodium nitroprusside-hemodiluted (e) mongrel dogs.
Figure 4B:
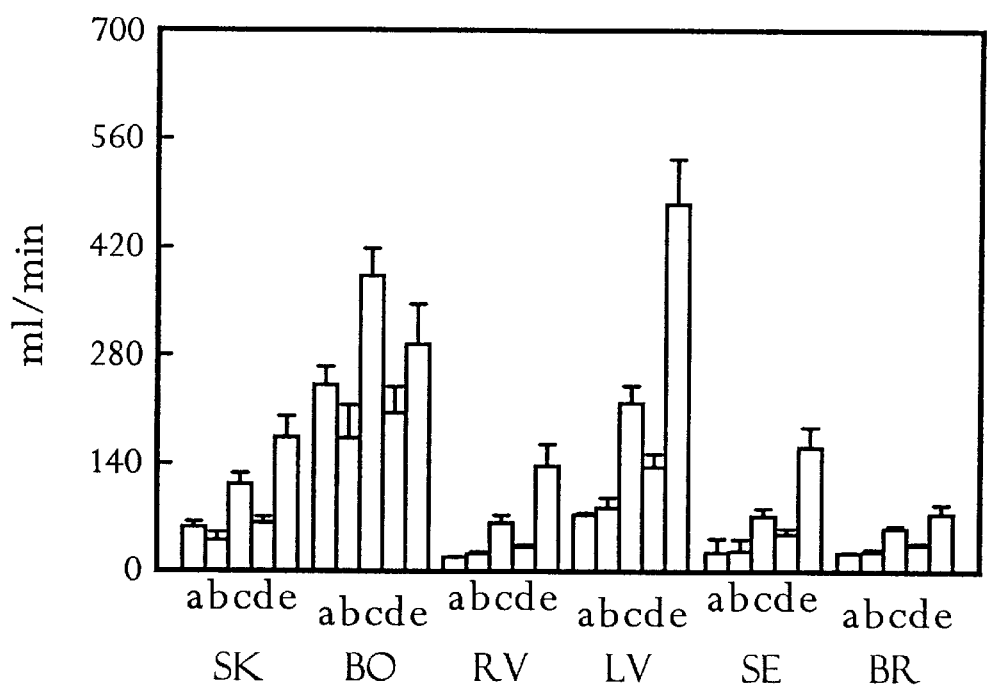
FIG. 4B is a bar graph representing the regional blood flows (ml/minute) in the skin (SK), bone (BO), right ventricle (RV), left ventricle (LV), septum (SE) and brain/cerebellum (BR) of control (a), sodium nitroprusside-treated (b), albumin-hemodiluted (c), hemoglobin-hemodiluted (d), and hemoglobin/sodium nitroprusside-hemodiluted (e) mongrel dogs.

Compared to control and post-SNP infusion blood flows, regional blood flows after hemodilution with albumin were significantly increased (about 80%) through various organ beds (see FIGS. 4A–4B). The increased flows in the kidney, GI tract (stomach, small and large intestine, colon), liver (hepatic artery), lung (bronchial), skeletal muscle, skin, bone and brain were in approximate proportion to the increased cardiac output (see FIGS. 5A–5B). There was, however, a redistribution of flow during hemodilution from the spleen, which received a smaller fraction of the cardiac output, to the heart which received a greater fraction of the cardiac output (see FIGS. 5A–5B).

Effects of Hemodilution with Hemoglobin

When hematocrit was reduced to 50% of control during hemodilution with hemoglobin, cardiac output and stroke volume did not change from control values (see FIGS. 1A–1D).

Similar to hemodilution with albumin, systemic pressures were not changed from control values (see FIGS.

TABLE 5

| Parameter | Control | SNP | AbHD | HbHD | HbHD + SNP |
|---|---|---|---|---|---|
| Norepinephrine pg/ml, n = 8 | 114 ± 7 | — | 106 ± 6 | 125 ± 12 | 102 ± 14 |
| Epinephrine pg/ml, n = 8 | 217 ± 18 | — | 249 ± 19 | 219 ± 14 | 252 ± 22 |
| Lactate meq/L, n = 6 | 1.4 ± 0.2 | — | — | 2.2 ± 0.3 | 2.7 ± 0.4 |
| Cyanide mg/L, n = 6 | — | — | — | 0.13 ± 0.03 | 0.46 ± 0.04 |

2A–2D and Table 2). Despite a decrease in apparent viscosity similar to albumin hemodilution (assumed 50% of control), systemic vascular resistance was not changed from control values, however, systemic vascular hindrance increased almost 100% (see FIGS. 3A–3B). Left ventricular elastance and other hemodynamic parameters were not changed from control values. Thus, stroke volume and cardiac output were not increased because the decreased viscosity component of afterload was offset by the increased hindrance component (SVH).

Whole blood hemoglobin concentration decreased only 22% during hemodilution with hemoglobin (from 14.7±0.3 to 11.5±0.5 g/100 ml). Plasma hemoglobin (4.6 g/100 ml) comprised approximately 40% the total whole blood hemoglobin concentration (see Table 2). Arterial oxygen content decreased only 24% (from 19.7±0.4 to 14.9±0.4 ml/100 ml) (see Table 4). Despite the additional oxygen supplied by plasma hemoglobin, hemodilution and the unchanged cardiac output resulted in a 30% decrease in oxygen delivery. However, a 60% increase in oxygen extraction ratio maintained oxygen consumption at baseline levels (Table 4). Arterial pH, electrolytes and plasma catecholamines were unchanged from control levels.

Total blood methemoglobin was not changed significantly from control, although the infused hemoglobin (plasma) had a greater percentage of methemoglobin (see Table 2). The plasma methemoglobin level was not significantly different from that of the purified hemoglobin product. Arterial blood gases and electrolytes remained within the control range. Again, similar to the albumin solution, the hyperoncotic hemoglobin solution caused plasma colloid osmotic blood pressure to increase approximately 22% yet there was no significant change in blood volume (see Tables 2 and 3). Some plasma hemoglobin dissociation was evident by the presence of hemoglobin in the urine (hemoglobinuria). The amount excreted varied but was always less than 1% of the approximately 100 grams hemoglobin infused.

Changes in regional blood flows were measured and the results are presented below in Table 6. (See also FIGS. 4A–4B)

TABLE 6

| ORGAN BLOOD FLOW | CHANGE FROM CONTROL |
|---|---|
| Renal | No |
| Gastrointestinal | No |
| Spleen | Yes (−39%) |
| Pancreas | No |
| Liver | No |
| Lung | Yes (−53%) |
| Skin | No |
| Bone | No |
| Skeletal muscle | No |
| Myocardium | Yes (+80%) |
| Brain | Yes (+40%) |
| Total (= Cardiac output) | No |

Thus, as described previously, in contrast to hemodilution with albumin, hemodilution with hemoglobin product did not augment cardiac output. As Table 6 shows, though, a fraction of cardiac output going to the spleen and lung was redistributed to the heart and brain. (See also FIGS. 5A–5B)

Hemodilution with Hemoglobin in Combination with SNP

The SNP dose (≈2 μg/kg/min i.v.) tested before hemodilution was completely ineffective following hemodilution with hemoglobin. Two-way ANOVA revealed a significant interaction between hemoglobin hemodilution and SNP. Larger SNP doses (54.2±4.6 μg kg$^{-1}$ min$^{-1}$ i.v.) were needed to decrease MAP only 18% (see Table 2). However, during this infusion cardiac output increased to approximately 180% of control values (see FIGS. 1A–1D). Proportional increases occurred in stroke volume as heart rate did not change.

In contrast to SNP infusion before hemoglobin hemodilution, SNP infusion during hemoglobin hemodilution had no effect on preload (LVEDP) or right atrial pressure (see FIGS. 2A–2D). Systemic vascular resistance and hindrance decreased about 50% from hemoglobin hemodilution to values similar to albumin hemodilution (FIGS. 3A–3B). Thus, although a decreased vascular component (MAP) of afterload was evident, the increased stroke volume and cardiac output during hemoglobin hemodilution along with SNP were primarily due to an unmasking of the reduced viscosity component of afterload as seen with albumin hemodilution.

Compared to hemoglobin hemodilution alone, during hemoglobin hemodilution along with SNP, oxygen delivery increased and extraction ratio decreased thereby returning to control values (see Table 4). Oxygen consumption was unchanged. Arterial hemoglobin, methemoglobin, pH, electrolytes, plasma catecholamines, and lactate levels were not significantly different from hemoglobin hemodilution values (see Tables 3 and 5). Blood cyanide levels were elevated but did not reach toxic concentrations (see Table 4).

Similar to albumin hemodilution, regional blood flows after hemoglobin hemodilution in combination with SNP infusion were significantly increased through various organ beds as is indicated below in Table 7. (See also FIGS. 4A–4B)

TABLE 7

| ORGAN BLOOD FLOW | CHANGE FROM CONTROL |
|---|---|
| Renal | No |
| Gastrointestinal | Yes (+80%) |
| Spleen | No |
| Pancreas | Yes (+80%) |
| Liver | Yes (+80%) |
| Lung | Yes (+80%) |
| Skin | Yes (+80%) |
| Bone | Yes (+80%) |
| Skeletal muscle | Yes (+80%) |
| Myocardium | Yes (+200%) |
| Brain | Yes (+80%) |
| Total (= Cardiac output) | Yes (+80%) |

As is shown in Table 7, cardiac output was augmented by hemodilution with hemoglobin in combination with SNP. In this study, for about every ten molecules of hemoglobin, about one molecule of nitric oxide in the form of SNP was required to increase cardiac output for the short duration (30 minutes) studied.

Figure 5A:
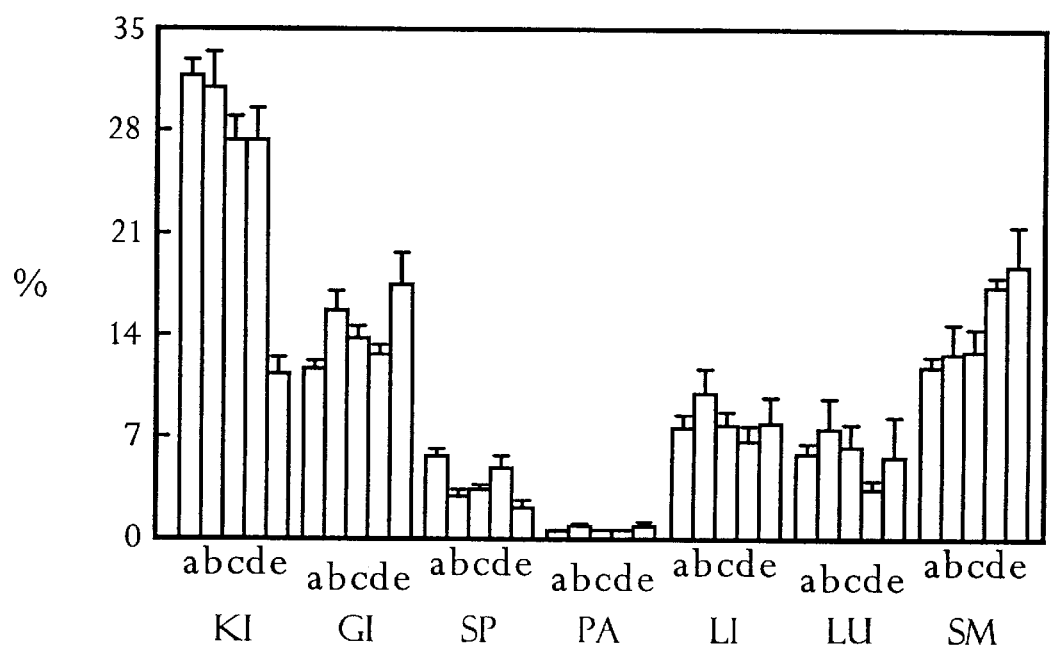
FIG. 5A is a bar graph representing the fractional distribution of cardiac output (%) in the kidney (KI), gastrointestinal tract (GI), spleen (SP), pancreas (PA), liver/hepatic arteries (LI), lung/bronchial arteries (LU) and skeletal muscle (SM) of control (a), sodium nitroprusside-treated (b), albumin-hemodiluted (c), hemoglobin-hemodiluted (d), and hemoglobin/sodium nitroprusside-hemodiluted (e) mongrel dogs.
Figure 5B:
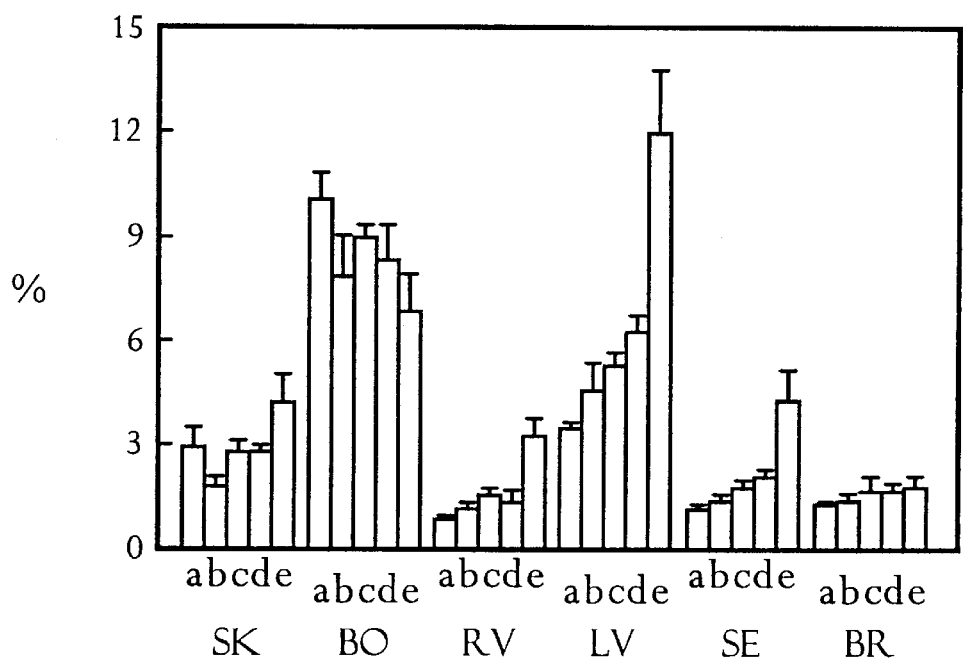
FIG. 5B is a bar graph representing the fraction distribution of cardiac output (%) in the skin (SK), bone (BO), right ventricle (RV), left ventricle (LV), septum (SE) and brain/cerebellum (BR) of control (a), sodium nitroprusside-treated (b), albumin-hemodiluted (c), hemoglobin-hemodiluted (d), and hemoglobin/sodium nitroprusside-hemodiluted (e) mongrel dogs.

The increased blood flows in the GI tract, pancreas, liver, lung, skin, bone and brain were in approximate proportion to the increased cardiac output and thus the fraction of cardiac output to these organs was not changed from control values (see FIGS. 5A–5B). There was, however, a redistribution of flow from the kidney and spleen which received smaller fractions of the cardiac output, to the skeletal muscle and heart which received a greater fraction of the cardiac output (See FIGS. 5A–5B). Left ventricular myocardial flow increased to almost 500 ml/minute indicating near maximal vasodilation of the coronary arteries.

Because cyanide is released during SNP metabolism the toxicity of this compound was a concern. Whole blood levels of cyanide (0.46 mg/L) in the present study did not reach toxic levels despite doses of SNP (0.8 to 1.4 mg/kg per 30 minutes) that were near those reported to be dangerous in Michenfelder, *Anesthesiology*, 62, 415–421 (1985). Vasey et al., *Anesthesiology*, 62, 415–421 (1985) describes the infusion a similar SNP dose (50.0 μg/kg/min or 1.5 mg/kg/30 minutes) and detected approximately 1.8 mg/L whole blood cyanide. Consistent with lower plasma cyanide levels, our dogs did not exhibit the severe acidosis (arterial pH −7.18±0.02) or elevated plasma lactate caused by doses of SNP greater than 1.0 mg/kg.

EXAMPLE II

To gain more direct evidence that the molecular mechanism governing the hemodynamic pharmacology of hemoglobin-hemodilution involves inactivation or antagonism of NO, we conducted a study on systemic guanosine 3′:5′-cyclic monophosphate (cyclic GMP) production. Cyclic GMP is the end-product of the L-arginine→NO synthase→NO→ guanylate cyclase→cyclic GMP pathway. In a series of dog studies using the methods described in Example 1, plasma from arterial blood samples was examined for cGMP concentrations before and after hemodilution with either albumin (Ab-HD or oxyhemoglobin (oxyHb-HD). In Table 8, hemodilution caused an increase in plasma cGMP levels, however, the response was significantly attenuated in oxyHb-HD.

TABLE 8

| | Condition | Plasma cGMP [μg/ml] |
|---|---|---|
| n = 5 | Control | 9.04 ± 0.62 |
| | Ab-HD | 23.78 ± 1.14* |

TABLE 8-continued

|  | Condition | Plasma cGMP [μg/ml] |
|---|---|---|
| n = 5 | Control | 9.76 ± 0.70 |
|  | oxyHb-HD | 17.22 ± 1.02*† | values are mean ± sem. *, P < 0.05 from respective control. †, from Ab-HD.

The data suggests that as blood is diluted, a signal triggers the release of nitric oxide with subsequent cGMP formation. It is not clear whether the signal is a humoral substance in plasma or a physical component such as $PO_2$, $PCO_2$, viscosity, etc. However, the physiological significance of increased cGMP formation may be to facilitate increases in blood flow via arteriolar dilation. Since oxyHb-HD and Ab-HD dilute blood to the same extent, the attenuated cGMP formation in oxyHb-HD must be due oxyHb mediated interference with nitric oxide synthase, NO directly or guanylate cyclase activity.

The effects of administering a nitric oxide donor/cyclic GMP generator (Na nitroprusside) on plasma cyclic GMP levels and arterial blood pressure are shown in Table 9 for control (non-hemodiluted), Ab-HD and oxyHb-HD animals.

TABLE 9

|  | Condition | Plasma cGMP [μg/ml] | MAP, mm Hg |
|---|---|---|---|
| n = 5 | Control | 9.11 ± 0.55 | 160 ± 9 |
|  | ≈2 μg/kg/min SNP | 13.06 ± 0.82* | 121 ± 6* |
|  | ≈8 μg/kg/min SNP | 17.80 ± 0.94* | 80 ± 5* |
| n = 5 | Ab-HD | 23.78 ± 1.14 | 138 ± 8 |
|  | ≈4 μg/kg/min SNP | 24.28 ± 1.22 | 75 ± 3* |
| n = 5 | oxyHb-HD | 17.22 ± 1.02 | 142 ± 6 |
|  | ≈50 μg/kg/min SNP | 26.44 ± 1.76* | 127 ± 9 | values are mean ± sem. *, P < 0.05 from control, Ab-HD or oxyHb-HD

In the control studies (non-hemodiluted), therapeutic doses of SNP produced inverse but proportional changes in plasma cGMP and mean arterial pressure. Clearly, the hypotension was mediated by vasodilation induced by the cGMP formed as a result of nitric oxide release from SNP. In Ab-HD, however, SNP caused a similar hypotension but no additional increase in plasma cGMP concentration. The obvious question is: why was spillover of CGMP to the plasma maximized during Ab-hemodilution alone? In the case of oxyHb-HD, additional spillover of CGMP was evident when large but non-therapeutic SNP doses were administered. Again, it is not clear where in the NO→cGMP pathway does oxyHb exert its inhibitory effect.

In a small pilot study, we investigated the possibility that oxyHb would cause selective differences in regional cGMP production (Table 10). An in vivo method that is based on direct microdialysis of the organ tissue was used to examine the regional interstitial production of cGMP. The microdialysis technique uses a small dialysis fiber (250 μm diameter) that is inserted into the tissue and perfused to sample extracellular metabolites.

TABLE 10

Cyclic GMP levels (μg/ml) in regional interstitial microdialysate before hemodilution (CTRL), during hemodilution with either albumin (AbHD) or hemoglobin (HbHD), and then during a subsequent infusion of Na nitroprusside (2 and 50 μg/kg/min, respectively).

| (n =0 4) | KI | GI | SP | LI | LU | MU | BO | HE | BR |
|---|---|---|---|---|---|---|---|---|---|
| CTRL | 9.42 | 6.56 | 12.58 | 7.74 | 10.48 | 11.32 | 9.14 | 7.80 | 13.28 |
|  | ±0.96 | 1.10 | 1.78 | 0.98 | 1.96 | 1.60 | 1.00 | 0.92 | 1.36 |
| Ab | 20.54* | 18.12* | 22.60* | 14.24* | 22.46* | 22.24* | 18.12* | 21.56* | 24.16* |
|  | ±1.68 | 1.50 | 2.18 | 1.66 | 2.92 | 1.52 | 1.50 | 2.08 | 1.22 |
| SNP | 24.24* | 27.78*† | 21.60* | 18.96* | 23.64* | 24.81* | 26.08*† | 24.59* | 26.76* |
|  | ±4.74 | 1.95 | 2.90 | 3.48 | 4.96 | 1.49 | 2.18 | 3.40 | 4.32 |

| (n = 4) | KI | GI | SP | LI | LU | MU | BO | HE | BR |
|---|---|---|---|---|---|---|---|---|---|
| CTRL | 9.71 | 5.00 | 10.36 | 8.82 | 9.88 | 10.70 | 9.00 | 7.54 | 13.62 |
|  | ±0.72 | 0.50 | 0.94 | 1.04 | 1.12 | 1.18 | 0.94 | 0.66 | 0.48 |
| Hb | 17.51* | 12.68* | 16.40* | 20.34* | 18.74* | 17.98* | 18.64* | 14.44* | 19.94* |
|  | ±1.58 | 1.14 | 1.32 | 1.94 | 2.02 | 1.30 | 1.72 | 2.11 | 1.76 |
| SNP | 28.36*† | 23.26*† | 19.38* | 22.78* | 26.38* | 24.40*† | 18.48* | 20.20*† | 27.65*† |
|  | ±2.93 | 2.22 | 1.16 | 2.63 | 1.89 | 1.66 | 2.65 | 1.29 | 3.73 |

KI, kidney; GI, gastrointestinal tract; SP, spleen; LI, liver; LU, lung; BO, bone; HE, heart; BR, brain. Values are mean ± SE.
*P < 0.05 vs. control;
† P < 0.05 vs. respective HD.

With exception of GI tract and brain, there were no significant differences in cGMP levels between organ beds. With greater sample sizes it can be estimated that more regional difference will be evident. In general, the regional interstitial data were not remarkably different from the plasma measurements.

We conducted a separate pilot study to test if administration of a nitric oxide synthase inhibitor (L-nitro arginine methyl ester, i.e. L-NAME) during Ab-HD would cause hemodynamics and cGMP production to mimic oxyHb-HD. Approximately 6 mg/kg L-NAME was administered i.v. bolus during Ab-HD. Significant increases in MAP and decreases in plasma cGMP were evident (Table 11).

TABLE 11

|  | cGMP, μg/ml | MAP, mm Hg | CO, ml/min |
|---|---|---|---|
| Control | 8.74 ± 0.70 | 134 ± 6 | 2201 ± 134 |
| Ab-KD | 22.04 ± 1.01* | 126 ± 6 | 3710 ± 255* |
| L-NAME | 17.38 ± 0.98*† | 152 ± 8*† | 2413 ± 1721† |

TABLE 11-continued

| | cGMP, µg/ml | MAP, mm Hg | CO, ml/min |
|---|---|---|---| n = 3 in each group; values are mean ± sem. *, P < 0.05 from control; †, from Ab-HD; L-NAME = 6 mg/kg/min Cardiac output was also returned to control (pre-hemodilution) levels. These results support our hypothesis that the unchanged cardiac output of oxyHb-HD is caused by interference of the NO-cGMP system. However, it was not clear where in the NO→cGMP pathway does oxyHb cause inactivation.

In another pilot study, we examined if infusion of a nitric oxide substrate (N-benzoyl-L-arginine ethyl ester, i.e. BAEE) would override the hypothesized NO scavenging by oxyHb and thereby mimic Ab-HD hemodynamics and CGMP production shown in Tables 8–11. While BAEE administration increased plasma cGMP levels and caused significant vasodilation as evidenced by the decreased mean arterial pressure, cardiac output was not increased (Table 12).

TABLE 12

| | cGMP, µg/ml | MAP, mm Hg | CO, ml/min |
|---|---|---|---|
| Control | 8.56 ± 0.80 | 143 ± 7 | 2978 ± 134 |
| oxyHb-HD | 17.80 ± 0.95* | 146 ± 5 | 2880 ± 245 |
| BAEE | 24.44 ± 1.05*† | 108 ± 8*† | 2376 ± 233 | n = 3; values are mean ± sem. *, P < 0.05 from control. †, from oxyHb-HD; BAEE = 200–400 µg/kg/min Comparing these results to those obtained with SNP administration (see Example 1 and Tables 8–11), it becomes apparent that oxyHb selectively is more potent at opposing NO-CGMP activation by SNP in venous relative to arteriolar beds. In other words, SNP was able to reduce the arteriolar afterload produced by oxyHb-mediated arteriolar constriction but did not affect oxyhb-mediated venoconstriction or preloading. Hence, cardiac output increased. This is atypical of SNP, which classically dilates both venous and arteriolar beds with little effect on cardiac output. Whereas in the case of BAEE administration, oxyHb caused relatively little opposition to arterial or venous dilation by BAEE. This was evidenced by the decreased MAP and unchanged cardiac output (Table 12). It may that the high membrane permeability of BAEE was responsible for its unimpeded participation in cGMP formation (Table 12). Different More unexpected results were obtained when BAEE was used to reverse the effects of L-NAME in AB-HD dogs. With BAEE, the original hemodynamics of Ab-HD alone were expected to be evident, i.e., increased cardiac output. This was not the case, cardiac output was not reversed to the high levels of Ab-HD alone. These data and the hemoglobin-BAEE evidence suggest that hemoglobin may bind or antagonize to a greater extent the guanylate cyclase receptor in arteries compared to veins. The exact mechanism is not obvious. Nor, is the method of reversing hemoglobin mediated effects on cardiac output obvious to one skilled in the art.

EXAMPLE III

Hemodilution with oxyhemoglobin colloid (oxyHb) produces a vasoconstriction that attenuates cardiac output (CO) and oxygen delivery ($DO_2$). The vasoconstriction is caused by an interference of guanylate cyclase activity and is selectively greater in veins compared to arteries. Vasodilators that potentiate guanylate cyclase activity preferentially in arteries compared to veins sustain preload but reduce afterload and, hence, increase CO and maximize $DO_2$ of oxyHb-hemodilution. Dihydropyridine compounds are classically calcium channel antagonists but are now discovered to "from oxyHb-HD; BAEE=200–400 µg/kg/min" these compounds have varying terminal half-life eliminations (t½ in hours) they may provide a time-controlled superaugmentation of CO and $DO_2$ during hemodilution with hemoglobin products.

Anesthetized dogs were isovolemically hemodiluted to ≈20% Hct with 10% oxyHb combined physically, or infused separately, with dihydropyridine compounds (DHP) of varying t½ (hours): DHP(≈8–14 h), DHP(≈14–24 h) and DHP (≈24–45 h). The end point was to minimize the amount of each compound needed to reduce oxyHb arteriolar constriction (evidenced by a ↓ in mean BP) while increasing cardiac output ≈50% or more (comparable to albumin-hemodilution). Systemic hemodynamics and guanylate cyclase activity (cyclic GMP formation) in mixed venous blood are reported during baseline and following hemodilution.

TABLE 13

Effect of hemodilution with oxyHb-dihydropyridine compositions on systemic hemodynamics and blood cyclic GMP formation.

| | Baseline | oxyHbDHP (8–14 h) | oxyHbDHP (14–24 h) | oxyHbDHP (24–45 h) |
|---|---|---|---|---|
| [DHP] | | ≈ 100 µg | ≈ 100 µg | ≈ 5000 µg |
| Duration | | 0.5–1 hour | 1–2 hours | 2–4 hours |
| MAP, mmHg | 143 ± 6 | 118 ± 3* | 115 ± 4* | 140 ± 8 |
| HR, b/min | 135 ± 9 | 114 ± 4* | 112 ± 4* | 128 ± 10* |
| CO, ml/min | 2510 ± 194 | 4353 ± 182* | 4066 ± 144* | 4741 ± 228* |
| SV, ml | 18.9 ± 1.6 | 38.9 ± 2.4* | 36.6 ± 1.8* | 37.4 ± 2.0* |
| cGMP, ng/min | 268 ± 34 | 758 ± 58* | 937 ± 89* | 587 ± 26* | n = 6 in each DHP group; values are mean ± sem; *, P < 0.05 vs. respective baseline.

All three classes of oxyHb-DHP compositions increased CO durations somewhat proportional to their elimination half-life. However, the relatively short duration of effects for these long-acting DHP compounds suggests that oxyHb may compete for a site near the calcium channel receptor. The significant increase in mixed venous cGMP also supports a partial mechanism of DHP pharmacology that involves activation of the cGMP pathway, a result especially important to reversing oxyHb vasoconstriction. These studies suggest that the oxyHb-DHB compositions provide a range of time-controlled superaugmentation of CO, and consequently $^0DO_2$, which could be applied to specific patients, i.e., shorter duration compositions for trauma-related blood replacement and longer durations for blood conservation in surgical procedures.

What is claimed is:

1. A method for controlling intravascular blood flow and blood oxygen delivery to tissues of a body of a human or animal subject, comprising:
   intravenously administering an effective amount of an oxygen containing hemoglobin blood substitute to said subject; and
   administering to said subject an effective amount of a cyclic guanosine monophosphate-generating compound for a time and under conditions effective to alter blood flow and oxygen to said tissues a hemoglobin blood substitute to said subject; and
   administering to said subject a cyclic guanosine monophosphate-generating compound.

2. The method of claim 1, wherein said administration to said subject effects arterial dilation to a greater extent than venous dilation.

3. The method of claim 1, wherein said administration to said subject effects increased stroke volume.

4. The method of claim 1, wherein cardiac output of oxygenated blood in said subject is increased.

5. The method of claim 1, wherein said administration effects reversal of hemoglobin-derived antagonism of cyclic GMP generation.

6. The method of claim 1, wherein said blood flow and oxygen delivery have rates that are time-controlled.

7. The method of claim 1 wherein said administration of said hemoglobin and cyclic GMP-generating compound provides reduced vasoconstriction in said subject.

8. The method of claim 1, wherein blood flow in one or more regions of the body increases following said administration of cyclic GMP-generating compound and said hemoglobin substitute.

9. The method of claim 8, wherein said one or more regions of the body are selected from the group consisting of the gastrointestinal organs, pancreas, liver, lung, skin, bone, skeletal muscle, myocardium and brain.

10. The method of claim 1 wherein said cyclic GMP-generating compound is chemically coupled to said hemoglobin.

11. The method of claim 10, wherein said chemical coupling comprises binding of said cyclic GMP-generating compound to lysine residues, glutamate residues or thiolated amino groups on hemoglobin.

12. The method of claim 1 wherein said cyclic GMP-generating compound is selected from the group consisting of dihydropyridines, nitric oxide donors, nitric oxide precursors, nitric oxide releasers, and cyclic GMP analogs.

13. The method of claim 12 wherein said cyclic GMP-generating compound is selected from the group consisting of sodium nitroprusside, organic nitrates, S-nitrosothiols, syndonimines, furoxanes, and nitrovasodilator-dihydropyridine hybrids.

14. The method of claim 12 wherein said cyclic GMP-generating compound is selected from the group consisting of L-arginine, N-benzoyl-L-arginine ethyl ester, N-substituted arginine analogs, lysine, glutamate and ornithine.

15. The method of claim 12 wherein said cyclic GMP-generating compound is selected from the group consisting of acetylcholine, bradykinin, adenine nucleotides, dihydropyridines and nitrovasodilator-dihydropyridine hybrids.

16. A method for controlling intravascular blood flow and blood oxygen delivery to tissues of a body of a human or animal subject, comprising:

intravenously administering an effective amount of an oxygen containing hemoglobin blood substitute to said subject; and administering to said subject an effective amount of a nitric oxide-associated compound for a time and under conditions effective to alter blood flow and oxygen to said tissues.

17. The method of claim 16, wherein said administration to said subject effects arterial dilation to a greater extent than venous dilation.

18. The method of claim 16, wherein said administration to said subject effects increased stroke volume.

19. The method of claim 16, wherein cardiac output of oxygenated blood in said subject is increased.

20. The method of claim 16, wherein said administration effects reversal of hemoglobin-derived antagonism of nitric oxide.

21. The method of claim 16, wherein said blood flow and oxygen delivery have rates that are time-controlled.

22. The method of claim 16 wherein said administration of said hemoglobin and nitric oxide-associated compound reverses vasoconstriction in said subject.

23. The method of claim 16, wherein blood flow in one or more regions of the body increases following said administration of nitric oxide-associated compound and said hemoglobin substitute.

24. The method of claim 23, wherein said one or more regions of the body are selected from the group consisting of the gastrointestinal organs, pancreas, liver, lung, skin, bone, skeletal muscle, myocardium and brain.

25. The method of claim 16 wherein said nitric oxide-associated compound is chemically coupled to said hemoglobin.

26. The method of claim 25 wherein said chemical coupling comprises binding of said nitric oxide-associated compound to lysine residues, glutamate residues or thiolated amino groups on hemoglobin.

27. The method of claim 16 wherein said nitric oxide-associated compound is a nitric oxide precursor, nitric oxide donor, or nitric oxide releaser.

28. The method of claim 27 wherein said nitric oxide-associated compound is selected from the group consisting of L-arginine, N-benzoyl-L-arginine ethyl ester, N-substituted arginine analogs, lysine, glutamate, and ornithine.

29. The method of claim 27 wherein said nitric oxide-associated compound is selected from the group consisting of sodium nitroprusside, organic nitrates, S-nitrosothiols, syndonimines, fuoxans, and nitrovasodilator-dihydropyridine hybrid structures.

30. The method of claim 27 wherein said nitric oxide-associated compound is selected from the group consisting of acetylcholine, bradykinin, adenine nucleotides, dihydropyridines and nitrovasodilator-dihydropyridine hybrids.

* * * * *